US008716182B2

(12) United States Patent
Schlotterbeck et al.

(10) Patent No.: US 8,716,182 B2
(45) Date of Patent: *May 6, 2014

(54) LIQUID AQUEOUS CROP PROTECTION FORMULATIONS

(75) Inventors: Ulf Schlotterbeck, Mannheim (DE); Claude Taranta, Stutensee (DE); Ralf Lurtz, Altrip (DE); Jurith Montag, Limburgerhof (DE)

(73) Assignee: BASF SE, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/122,790

(22) PCT Filed: Oct. 9, 2009

(86) PCT No.: PCT/EP2009/063196
§ 371 (c)(1),
(2), (4) Date: Apr. 6, 2011

(87) PCT Pub. No.: WO2010/040834
PCT Pub. Date: Apr. 15, 2010

(65) Prior Publication Data
US 2011/0195839 A1 Aug. 11, 2011

(30) Foreign Application Priority Data

Oct. 10, 2008 (EP) ..................... 08166374

(51) Int. Cl.
*A01N 25/00* (2006.01)
(52) U.S. Cl.
USPC ...................................... 504/116.1
(58) Field of Classification Search
None
See application file for complete search history.

(56) References Cited

U.S. PATENT DOCUMENTS

| 3,666,785 | A | 5/1972 | Sakai et al. |
| 4,272,920 | A | 6/1981 | Dawson |
| 4,283,222 | A | 8/1981 | Horide et al. |
| 4,541,860 | A | 9/1985 | Civilla et al. |
| 4,945,100 | A | 7/1990 | Nyfeler et al. |
| 4,973,352 | A | 11/1990 | Heinrich et al. |
| 5,045,311 | A | 9/1991 | Pinter et al. |
| 5,192,793 | A | 3/1993 | Szekely et al. |
| 5,334,585 | A | 8/1994 | Derian et al. |
| 5,459,122 | A | 10/1995 | Ford et al. |
| 5,869,517 | A | 2/1999 | Muller et al. |
| 5,911,915 | A | 6/1999 | Fonsny et al. |
| 6,383,984 | B1 | 5/2002 | Aven |
| 6,455,471 | B1 | 9/2002 | Gubelmann-Bonneau et al. |
| 6,494,082 | B1 | 12/2002 | Mizobe |
| 6,602,823 | B1 | 8/2003 | Röchling et al. |
| 6,664,213 | B1 | 12/2003 | Furusawa et al. |
| 6,737,553 | B1 | 5/2004 | Maas et al. |
| 6,838,473 | B2 | 1/2005 | Asrar et al. |
| 7,256,317 | B2 | 8/2007 | Maas et al. |
| 2002/0098221 | A1 | 7/2002 | Taranta et al. |
| 2004/0157745 | A1 | 8/2004 | Vermeer et al. |
| 2005/0215433 | A1 | 9/2005 | Benitez et al. |
| 2007/0066489 | A1 | 3/2007 | Vermeer et al. |
| 2008/0153706 | A1 | 6/2008 | Frisch et al. |
| 2008/0214683 | A1 | 9/2008 | Steinbrenner et al. |
| 2008/0234350 | A1 | 9/2008 | Ziegler et al. |
| 2010/0137375 | A1 | 6/2010 | Finch |
| 2010/0210461 | A1 | 8/2010 | Stoesser et al. |
| 2010/0227763 | A1 | 9/2010 | Krapp et al. |
| 2010/0234227 | A1* | 9/2010 | Maier et al. ................... 504/138 |
| 2010/0234457 | A1 | 9/2010 | Taranta et al. |
| 2011/0039698 | A1 | 2/2011 | Taranta et al. |
| 2011/0105333 | A1 | 5/2011 | Israels et al. |
| 2011/0124590 | A1 | 5/2011 | Sowa et al. |
| 2011/0195846 | A1 | 8/2011 | Troppmann et al. |
| 2011/0224076 | A1 | 9/2011 | Sowa |

FOREIGN PATENT DOCUMENTS

| AU | 610388 | 11/1989 |
| CA | 2 068 826 | 11/1992 |
| CA | 1 334 274 | 2/1995 |
| CA | 2 570 358 | 1/2006 |
| DE | 69012487 | 2/1995 |
| DE | 198 57 963 | 6/2000 |
| EP | 0126430 | 11/1984 |
| EP | 0160182 | 11/1985 |
| EP | 0330904 | 9/1989 |
| EP | 0 341 126 | 11/1989 |

(Continued)

OTHER PUBLICATIONS

International Search Report, issued in PCT/EP2009/063196, dated Oct. 19, 2010.
International Preliminary Report on Patentability, issued in PCT/EP2009/063196, dated Jan. 5, 2011.
Karakotov et al., "Tebuconazole-Based Fungicidal Composition," Shchelkovo Agrokhim Stock Chem., Jun. 19, 2003, XP002498611.
Mulqueen, Patrick, J., et al., "Recent Developments in Suspoemulsions", Pestic. Sci., 1990, p. 451-465, vol. 29.
Rhee et al., "Formulation of Parenteral Microemulsion Containing Itraconazole," Arch. Pharm. Res., vol. 30, No. 1, 2007, pp. 114-123.

(Continued)

Primary Examiner — Alton Pryor
(74) Attorney, Agent, or Firm — Brinks Gilson & Lione

(57) ABSTRACT

The present invention relates to a novel liquid aqueous plant protection formulation which comprises
a) at least one organic plant protectant with a water solubility of less than 5 g/l at 20° C.;
b) at least one organic solvent with a water solubility of over 100 g/l at 20° C.;
c) at least one organic solvent with a water solubility of from 2 to 100 g/l at 20° C.;
d) at least one organic solvent with a water solubility of less than 2 g/l at 20° C.;
e) at least one nonionic surfactant;
f) at least one anionic surfactant; and
g) water.
The invention also relates to the use of the plant protection formulation for the treatment of plants and seed, to corresponding methods, and to treated seed.

20 Claims, No Drawings

(56) References Cited

FOREIGN PATENT DOCUMENTS

| | | |
|---|---|---|
| EP | 0432062 | 6/1991 |
| EP | 0505053 | 9/1992 |
| EP | 0 514 769 | 11/1992 |
| EP | 0728414 | 8/1996 |
| EP | 1 140 741 | 10/2001 |
| EP | 1339281 | 6/2002 |
| EP | 1347681 | 6/2002 |
| EP | 1702607 | 9/2006 |
| EP | 1886560 | 2/2008 |
| FR | 2609631 | 7/1988 |
| RU | 2238649 | 10/2004 |
| WO | WO 90/06681 | 6/1990 |
| WO | WO 9006681 * | 6/1990 |
| WO | WO 90/09103 | 8/1990 |
| WO | WO 9315605 | 8/1993 |
| WO | WO 96/01256 | 1/1996 |
| WO | WO 96/01305 | 1/1996 |
| WO | WO 99/66300 | 12/1999 |
| WO | WO 00/35278 | 6/2000 |
| WO | WO 00/78139 | 12/2000 |
| WO | WO 02/42488 | 5/2002 |
| WO | WO 02/43488 | 6/2002 |
| WO | WO 02/45507 | 6/2002 |
| WO | WO 0243488 * | 6/2002 |
| WO | WO 03/000053 | 1/2003 |
| WO | WO 03/022049 | 3/2003 |
| WO | WO 2005/105285 | 11/2005 |
| WO | WO 2006/002984 | 1/2006 |
| WO | WO 2006030006 | 3/2006 |
| WO | WO 2006/114186 | 11/2006 |
| WO | WO 2006/136357 | 12/2006 |
| WO | WO 2007/017501 | 2/2007 |
| WO | WO-2007028382 * | 3/2007 |
| WO | WO 2007028382 | 3/2007 |
| WO | WO 2007028387 | 3/2007 |
| WO | WO 2007028388 | 3/2007 |
| WO | WO 2007/057028 | 5/2007 |
| WO | WO 2007/110355 | 10/2007 |
| WO | WO 2008/017378 | 2/2008 |
| WO | WO 2008/043807 | 4/2008 |
| WO | WO 2008/061899 | 5/2008 |
| WO | WO 2009/019299 | 2/2009 |
| WO | WO 2009019299 * | 2/2009 |
| WO | WO 2009/133166 | 11/2009 |
| WO | WO 2010010005 | 1/2010 |
| WO | WO 2010/040835 | 4/2010 |
| WO | WO 2010/052178 | 5/2010 |

OTHER PUBLICATIONS

Shell Chemicals, "Methyl Proxitol Acetate," Mar. 16, 2007, XP007914204.

Skelton et al., "Formulation of Pesticide Microemulsions," Pesticide Formulations and Application Systems, vol. 8, 1988, pp. 36-45, XP002053622.

Tomšič et al., "Ternary Systems of Nonionic Surfactant Brij 35, Water and Various Simple Alcohols: Structural Investigations by Small-Angle X-ray Scattering and Dynamic Light Scattering," Journal of Colloid and Interface Science, vol. 294, 2006, pp. 194-211.

Office Action dated Jan. 31, 2012 from co-pending U.S. Appl. No. 12/671,744.

Herms et al., "Pyraclostrobin-more than just a fungicide", Phytomedizin, (2002), p. 18, vol. 32.

Office Action dated Mar. 20, 2013, from co-pending U.S. Appl. No. 13/123,142, filed Apr. 7, 2011.

* cited by examiner

LIQUID AQUEOUS CROP PROTECTION FORMULATIONS

This application is a National Stage application of International Application No. PCT/EP2009/063196, filed Oct.9, 2009, the entire contents of which are hereby incorporated herein by reference. This application also claims priority under 35 U.S.C. §119 to European Patent Application No. 08166374.2, filed Oct. 10, 2008, the entire contents of which are hereby incorporated herein by reference.

DESCRIPTION

The present invention relates to liquid aqueous plant protection formulations of one or more plant protectants, to the use of the plant protection formulations for the treatment of plants and seed, to corresponding methods, and to treated seed.

The protection of useful plants or crop plants from attack by plant-injurious organisms, the targeted control of the growth of useful plants, but also the control of harmful plants by the application of suitable plant protection compositions, are important instruments for increasing yields and thus also for safeguarding the production of plant-based foodstuffs.

Many plants, in particular useful plants, are extremely sensitive to attack by phytopathogenic fungi, bacteria, viruses, nematodes and insects during the phase before and after germination and emergence. This can be attributed firstly to the small size of the plant parts, which makes it difficult for the plant to compensate for damage. Secondly, the plant's natural defense mechanisms are frequently not yet developed at this early growth stage. Protecting the plant before and during germination is therefore an important instrument for reducing plant damage.

To avoid diseases of seed and seedlings, seed is treated with seed-dressing products prior to sowing, which products comprise plant protectants, usually fungicides, and frequently additionally other pesticides, in particular insecticides. Currently, organochemical fungicides and insecticides are mostly employed in the form of aqueous formulations, so that a good interaction with the target organism is ensured. However, many of these active substances are only sparingly soluble in water, or not at all, i.e. they have a water solubility of less than 5 g/l, frequently less than 1 g/l and in particular less than 0.1 g/l at 25° C. The preparation of stable formulations of pesticidal compounds which can be diluted readily with water is therefore a recurring problem.

Besides the stability of the formulation, other factors are also of great importance for applications for seed treatment. Thus, after application of the seed-dressing product, the seed should exhibit good flow behavior, so that aggregation or caking in the machinery during the seed-dressing process or during sowing is reduced, allowing high throughput rates. Moreover, low abrasion of the seed-dressing product is advantageous, since the reduced development of dust during the seed-dressing process or during sowing which this entails leads to improved work safety and environmental compatibility.

For seed dressing, organic pesticides with limited water solubility are frequently formulated as suspension concentrates or as emulsifiable concentrates, which are employed after dilution with water.

In emulsifiable concentrates, the active substance is present together with surface-active substances as a solution in an organic, water-immiscible solvent, typically a hydrocarbon mixture and/or a fatty acid methyl ester. The disadvantages are the use of large amounts of solvents which are frequently toxic, and the low stability upon dilution.

Suspension concentrates are formulations in which the active substance is present in the form of small, solid, for example finely ground, particles, which are suspended in aqueous dispersion media with the aid of surface-active substances. The task of the surface-active substances is to stabilize the active substance particles in the dispersion medium. However, the use of suspension concentrates frequently entails problems which are due to the fact that, upon storage over prolonged periods or at increased temperatures, the particles settle and their resuspension is very difficult, and that crystalline material forms during storage. As a consequence, these formulations are difficult to handle, and their biological activity may be inconsistent. Moreover, suspension concentrates are limited to active substances with a relatively high melting point. Moreover, many plant protectants are partially "deactivated" by water when formulated as a suspension concentrate.

While commercially available seed-dressing products which are based on aqueous suspension concentrates are more environmentally friendly than emulsifiable concentrates, they do not have the good applicational properties.

One alternative to suspension concentrates and emulsifiable concentrates are the microemulsions (ME). Microemulsions, also referred to as ME formulations in the case of active-substance-comprising microemulsions, are liquid multiphase systems consisting of water and at least one organic solvent which is not, or only sparingly, miscible with water, which systems comprise a disperse phase and a continuous phase, the disperse phase forming droplets or vesicles or else being capable of forming complex structures. In comparison with normal emulsions, the mean distance of the phase boundaries, as a rule the mean particle size or droplet size (Z=mean diameter determined by light scattering) of the disperse phase, in microemulsions is at least 5 times smaller, and is generally not more than 500 nm, in particular not more than 300 nm or even 200 nm, whereas the droplets in emulsions have a mean diameter in the μm range. A further distinguishing feature is that microemulsions are thermodynamically stable and form without the high energy input, which is required for emulsions. Due to the small particle size (droplet size) of the disperse phase, or of the complex channels, microemulsions are visually transparent.

Microemulsion formulations of organic pesticides are usually based on water and additionally comprise at least one surfactant and at least one cosolvent or cosurfactant, which is, as a rule, an organic solvent or a polyalkylene ether with a low molecular weight. Due to the high water content, the use of ME formulations reduces risks such as flammability, toxicity, negative impact on the environment, and costs, in comparison to emulsifiable concentrates (EC). As a consequence of the small particle size of the disperse phase, which comprises the active substance, it is moreover possible to achieve elevated bioavailability in many cases. However, it is difficult to formulate microemulsions of active substances which are sparingly soluble in water such that they have durable stability regarding droplet size, uniformity and the tendency of the active substance to crystallize. Moreover, the droplet size should remain stable even upon dilution with water, so that the biological activities of dilutions obtained from concentrated formulations are retained.

Microemulsion concentrates which comprise a hydrophobic agrochemical, an alkyl alkanoate as the first solvent, a polyhydric alcohol or a condensate of polyhydric alcohols as the second solvent and a surface-active agent are known from EP 1 347 681. The use of these concentrates in plant protection is only claimed in general terms, without specific applications, for example for the treatment of seed, being described.

WO 2006/030006 describes seed-dressing compositions based on microemulsions comprising the fungicide flutriafol, a surfactant system, an antifreeze agent and a water-insoluble liquid which is selected from among alkyl esters of lactic acids and dialkyl esters of adipic, glutaric and succinic acid. Compositions which go beyond this narrow scope are not mentioned.

WO 2007/028382, WO 2007/028387 and WO 2007/028388 disclose liquid formulations of triazole fungicides which comprise vegetable oil esters, at least one water-miscible polar-aprotic cosolvent and at least one water-immiscible cosolvent.

Thus, it was an object of the present invention to provide plant protection formulations which have advantageous seed-treatment properties for a wide range of active substances. In particular, it is intended that they are distinguished by high stability and homogeneous active substance distribution. In addition, it is intended that seed treated with these formulations has a good flow behavior and that the abrasion of the seed dressing is low.

Surprisingly, this object was achieved by the liquid aqueous plant protection formulations described hereinbelow.

The present invention therefore relates to a liquid aqueous plant protection formulation, preferably in the form of an aqueous microemulsion, which comprises
a) at least one organic plant protectant with a water solubility of less than 5 g/l at 20° C.;
b) at least one organic solvent with a water solubility of over 100 g/l, in particular at least 200 g/l or at least 300 g/l, at 20° C. (solvent b);
c) at least one organic solvent with a water solubility of from 2 to 100 g/l, in particular 3 to 90 g/l or 4 to 80 g/l, at 20° C. (solvent c);
d) at least one organic solvent with a water solubility of less than 2 g/l, in particular no more than 1 g/l or no more than 0.5 g/l, at 20° C. (solvent d);
e) at least one nonionic surfactant;
f) at least one anionic surfactant; and
g) water.

Accordingly, the present invention furthermore relates to the use of the plant protection formulations according to the invention for the treatment of plants or seed, and to corresponding methods. The present invention furthermore relates to seed which has been treated with such a plant protection formulation.

In particular, the formulations according to the invention provide stable aqueous formulations of organic, water-insoluble plant protectants, preferably fungicides, optionally in combination with further organic plant protectants, for the treatment of plants and seeds, preferably seed.

Typically, the formulations according to the invention are microemulsions, i.e. the components form a multi-phase system comprising at least one organic phase and one aqueous phase, the mean distances of the phase boundaries, as a rule the mean particle size or droplet size (Z=mean diameter determined by light scattering) of the disperse phase being in general not more than 500 nm. As opposed to suspension concentrates, the active substance is not in solid, but in dissolved form, in the formulations according to the invention. Therefore, the formulations according to the invention may also be referred to as ME formulations. The formulations according to the invention are stable liquid formulations which are visually transparent and do not tend to develop solids upon storage. Moreover, they remain liquid at temperatures down to below −10° C. without losing their advantageous properties. Their freezing temperature is usually below −10° C.

As a rule, the dynamic viscosity of the formulations according to the invention will not exceed a value of 0.5 Pa·s (at 20° C.) and is, at 20° C., frequently in the range of from 1 to 500 mPa·s and in particular in the range of from 2 to 200 mPa·s.

Moreover, the formulations according to the invention can readily be diluted with water. The formulations according to the invention can, for example before an application, simply be diluted with water, for example with 0.1 to 100 parts of water per part of the formulation, in particular 0.5 to 50 parts of water per part of the formulation, without coarsely-particulate material being formed. Frequently, the formulations according to the invention are employed in undiluted form or as a dilution with relatively small amounts of water, as a rule not more than 5 parts and preferably not more than 2 parts of water per part of the formulation. In this context, the quality of the water used for dilution is of minor importance, which means that for example tap water or spring water can be employed.

The average particle diameters mentioned herein represent Z averages of the particle diameters which can be determined by light scattering. Relevant methods with which the skilled person is familiar are described for example in H. Wiese (D. Distler, author), Wässrige Polymerdispersionen [Aqueous polymer dispersions], Wiley-VCH 1999, Chapter 4.2.1, p. 40ff, and in the literature cited therein; H. Auweter, D. Horn, J. Colloid Interf. Sci. 105 (1985), p. 399; D. Lilge, D. Horn, Colloid Polym. Sci. 269 (1991), p. 704 and H. Wiese, D. Horn, J. Chem. Phys. 94 (1991), p. 6429. As a result of the small particle size after dilution with water, the bioavailability, and thus the biological activity, is frequently increased in comparison with traditional formulations.

Frequently the formulations according to the invention are oil-in-water emulsions, where water, in which part of the solvents is dissolved (=aqueous phase), forms the continuous phase, while another part of the solvents and one or more plant protectants (=Oil phase) are present in the disperse phase. In some cases, however, they are water-in-oil emulsions, where water in which part of the solvents is dissolved (=aqueous phase) forms the discontinuous phase, while another part of the solvents and one or more plant protectants (=Oil phase) are present in the continuous phase. The formulations according to the invention may also be present as bicontinuous phases, i.e. the aqueous phase and the oil phase form mutually penetrating phases.

The terms "alkyl", "alkenyl", "alkylene", "aryl" used below are in each case collective terms for certain organic radicals. In this context, the prefix $C_n$-$C_m$ indicates in each case the total number of carbon atoms of the respective organic radical. In regard of the solvent, the prefix $C_n$-$C_m$ indicates in each case the total number of the carbon atoms of the respective organic solvent, with the exception of the N-methyl-substituted heterocyclic solvents such as N-methyllactams and N-methyl- or N,N-dimethylureas, where the prefix $C_n$-$C_m$ indicates in each case the total number of the carbon atoms of the heterocycle; also excepted are the trialkyl phosphates, where the prefix $C_n$-$C_m$, indicates the number of carbon atoms of the individual alkyl radicals.

The term "alkyl" refers to saturated straight-chain, branched or cyclic hydrocarbon radicals which have the number of carbon atoms stated in the prefix. Accordingly, ($C_1$-$C_7$)-alkyl refers to saturated straight-chain, branched or cyclic hydrocarbon radicals having 1 to 7 carbon atoms, such as, for example, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, cyclopentyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethyl-propyl, 1,2,2-trimethylpropyl, 1-ethyl-1-methylpropyl, 1-ethyl-2-methylpropyl, cyclohexyl, methylcyclopentyl, heptyl, 1-methylhexyl, 2-methylhexyl, 3-methylhexyl, 4-methylhexyl, 1,1,3-trimethylbutyl, 1,2-dimethylpentyl, 1,3-dimethylpentyl, 2,2-dimethylpentyl, 2,3-dimethylpentyl, 3,3-dimethylpentyl, 3,4-dimethylpentyl, 1-ethylpentyl, 2-ethylpentyl, 1,1,2-trimethylbutyl, 1,2,2-trimethylbutyl, 1-ethyl-1-methylbutyl, 1-ethyl-2-methylbutyl, methylcyclohexyl, 1,2-dimethylcyclopentyl, 1,3- dimethylcyclopentyl and ethylcyclopentyl.

The term "$C_2$-$C_4$-alkylene" refers to saturated, divalent straight-chain or branched hydrocarbon radicals having 2, 3 or 4 carbon atoms, such as, for example, ethane-1,2-diyl, propane-1,3-diyl, propane-1,2-diyl, 2-methylpropane-1,2-diyl, butane-1,4-diyl, butane-1,3-diyl (=1-methylpropane-1,3-diyl), butane-1,2-diyl and butane-2,3-diyl.

The term "aryl" refers to aromatic radicals including heteroaromatic radicals having 1 or 2 heteroatoms selected from among O and N, such as, for example, phenyl, naphthyl, anthracenyl, pyridyl, pyrryl, pyrazinyl, pyrimidinyl, purinyl, indolyl, quinolyl, isoquinolyl, imidazolyl, pyrazolyl, indazolyl, furyl, benzofuryl, isobenzofuryl, morpholinyl, oxazolyl, benzoxazolyl, isoxazolyl and benzisoxazolyl.

The formulations according to the invention comprise at least one solvent b) with a water solubility of over 100 g/l, in particular at least 200 g/l or at least 300 g/l, at 20° C. Solvent b) can be selected from among a multiplicity of polar organic solvents. It is preferably selected among hydroxylated ($C_4$-$C_8$)-alkanecarboxylic esters, aliphatic ($C_2$-$C_8$)-di- and -triols, in particular aliphatic ($C_5$-$C_8$)-di- and -triols, ($C_5$-$C_8$)-alkanecarboxylic alkoxyalkyl esters, dimethyl sulfoxide (DMSO), tetrahydrofurfuryl alcohol, ($C_3$-$C_4$)-alkylene carbonates, N,N'-dimethyl-($C_3$-$C_4$)-alkyleneureas, ($C_3$-$C_5$)-lactones, N-methyl-($C_3$-$C_5$)-lactams and tri-($C_1$-$C_3$)alkyl phosphates.

Within the scope of the present invention, the term "hydroxylated ($C_4$-$C_8$)-alkanecarboxylic esters" refers to esters of alkanecarboxylic acids which are esterified with alkanols, where either the alkyl radical originating from the acid or the alkyl radical originating from the alcohol is substituted by at least one hydroxyl group and where the total number of carbon atoms is 4 to 8. Examples of hydroxylated alkanecarboxylic acids are 5-hydroxyvaleric acid, 4-hydroxyvaleric acid, 2-hydroxyvaleric acid, 4-hydroxybutyric acid, 3-hydroxybutyric acid, 2-hydroxybutyric acid, 3-hydroxypropionic acid, lactic acid and hydroxyacetic acid. Examples of hydroxylated alkanols are pentane-1,5-diol, pentane-1,3-diol, pentane-2,4-diol, cyclopentane-1,2-diol, butane-1,4-diol, butane-2,3-diol, propane-1,2-diol, 2-(hydroxymethyl)butanol, 2-(hydroxyethyl)propanol, 2-(hydroxymethyl)propanol and ethane-1,2-diol. Examples of hydroxylated ($C_5$-$C_8$)-alkanecarboxylic esters are n-butyl 4-hydroxybutyrate, isobutyl 3-hydroxybutyrate, n-propyl 4-hydroxybutyrate, isopropyl 4-hydroxybutyrate, isopropyl 3-hydroxybutyrate, methyl 4-hydroxybutyrate, ethyl 4-hydroxybutyrate, 2-ethyl propyl lactate, 2-methylpropyl lactate, n-propyl lactate, isopropyl lactate, n-butyl lactate, isobutyl lactate, ethyl lactate, methyl lactate, cyclopentyl lactate, n-hexyl hydroxyacetate, cyclohexyl hydroxyacetate, 3-methylcyclopentyl hydroxyacetate, n-pentyl hydroxyacetate, 2-methylpentyl hydroxyacetate, n-butyl hydroxyacetate, tert-butyl hydroxyacetate, n-propyl hydroxyacetate, isopropyl hydroxyacetate, 5-hydroxypentyl acetate, 3-hydroxycyclopentyl propionate, 3-hydroxybutyl acetate, 3-hydroxypropyl acetate, 3-hydroxypentyl propionate, 3-hydroxycyclopentyl propionate, 2-hydroxymethylbutyl propionate, 3-hydroxypropyl propionate, 2-hydroxyethyl propionate, 2-hydroxymethylpropyl butyrate, 3-hydroxypropyl butyrate, 2-hydroxyethyl butyrate, 3-hydroxypropyl valerate and 2-hydroxyethyl valerate.

Within the scope of the present invention, aliphatic ($C_2$-$C_8$)-di- and -triols are understood as meaning aliphatic straight-chain or branched hydrocarbons having 2 to 8 and in particular 5 to 8 carbon atoms which have attached to them 2 or 3 hydroxyl groups, for example 1,5-pentanediol, 2,4-pentanediol, 2-methyl-2,4-pentanediol (hexylene glycol), 1,6-hexanediol, 2,5-hexanediol, 3-methyl-2,4-hexanediol, 1,7-heptanediol, 2,6-heptanediol, 1,8-octanediol, 2,7-octanediol, 1,3-cyclohexanediol, 1,2-cyclohexanediol, 1,4-cyclohexanediol, 1,2-cycloheptanediol 1,2,3-pentanetriol, 2,3,4-pentanetriol, 1,2,3-hexanetriol, 1,2,5-hexanetriol, 1,2,3-heptanetriol, 1,6,7-heptanetriol, 2,3,6-heptanetriol, 1,2,3-octanetriol, 2,3,4-octanetriol 1,2,8-octanetriol, 2,3,7-octanetriol, 1,2,3-cyclohexanetriol, 1,3,5-cyclohexanetriol, 1,2,4- cyclohexanetriol, 1,2,3-cycloheptanetriol and 1,2,6-cycloheptanetriol.

In the present context, ($C_5$-$C_8$)-alkanecarboxylic alkoxyalkyl ester is understood as meaning an ester of an alkanecarboxylic acid and an alkoxyalkanol, where the total number of carbon atoms is 5 to 8. Examples are isopropoxymethyl formate, ethylene glycol ethyl ether formate, ethylene glycol butyl ether formate, ethylene glycol 2-methylbutyl ether formate, ethylene glycol pentyl ether formate, isopropoxymethyl formate, isopropoxyethyl formate, isopropoxy-tert-butyl formate, ethoxymethyl acetate, isopropoxymethyl acetate, ethylene glycol methyl ether acetate, ethylene glycol ethyl ether acetate, ethylene glycol propyl ether acetate, ethylene glycol butyl ether acetate, ethylene glycol tert-butyl ether acetate, propylene glycol methyl ether acetate, propylene glycol ethyl ether acetate, propylene glycol propyl ether acetate, propylene glycol isopropyl ether acetate, methoxypropyl acetate, ethoxypropyl acetate, propoxypropyl acetate, isopropoxypropyl acetate, ethylene glycol methyl ether butyrate, ethylene glycol ethyl ether butyrate, propylene glycol methyl ether butyrate, propylene glycol methyl ether 2-methylpropylate, isopropoxymethyl butyrate, propoxymethyl tert-butyrate, methoxypropyl butyrate, methoxypropyl 2-methylpropylate, ethylene glycol methyl ether pentanoate and ethylene glycol methyl ether 3-methylbutyrate.

In the present context, ($C_3$-$C_4$)-alkylene carbonates refer to, in particular, cyclic diesters of carbonic acid with a total of 3 to 4 carbon atoms, such as, for example, ethylene carbonate, 1,3-propylene carbonate and 1,2-propylene carbonate.

Tri($C_1$-$C_3$)alkyl phosphates are understood as meaning the triesters of phosphoric acid with three ($C_1$-$C_3$)alkanols which are selected independently from one another, for example trimethyl phosphate, triethyl phosphate, tri-n-propyl phosphate, tri-isopropyl phosphate, tri-n-butyl phosphate, tri-isobutyl phosphate, methyl diethyl phosphate, dimethyl ethyl phosphate, methyl di-n-propyl phosphate, methyl ethyl n-propyl phosphate, ethyl 2-methylpropyl methyl phosphate and diethyl n-propyl phosphate.

An N,N'-dimethyl-($C_3$-$C_4$)alkyleneurea is understood as meaning di-N-methylated derivatives of cyclic ureas having 3 or 4 carbon atoms in the ring. An example of N,N'-dimethyl-($C_3$-$C_4$)alkyleneureas is N,N'-dimethylethyleneurea (1,3-dimethylimidazolin-2-one).

A ($C_3$-$C_5$)-lactone is understood as meaning a cyclic ester of a hydroxycarboxylic acid having 3, 4 or 5 carbon atoms in the ring. An example of ($C_3$-$C_5$)-lactones is γ-butyrolactone.

An N-methyl-($C_3$-$C_5$)-lactam is understood as meaning an N-methylated derivative of a lactam having 3, 4 or 5 carbon atoms in the ring. Examples of N-methyl-($C_3$-$C_5$)-lactams are N-methylpyrrolidone and N-methylpiperidone.

According to a preferred embodiment, the formulations according to the invention comprise at least one solvent b), which is selected among dimethyl sulfoxide, hydroxylated ($C_4$-$C_8$)-alkanecarboxylic esters, aliphatic ($C_5$-$C_8$)-di- and -triols, ($C_5$-$C_8$)-alkanecarboxylic alkoxyalkyl esters, tetrahydrofurfuryl alcohol, N-methyl-($C_4$-$C_5$)-lactams and ($C_4$-$C_5$)-lactones and which is in particular selected among γ-butyrolactone, dimethyl sulfoxide, methoxypropyl acetate, 2-methyl-2,4-pentanediol, hexylene glycol (1,6-hexanediol), tetrahydrofurfuryl alcohol and n-propyl lactate.

In an especially preferred embodiment, the formulations according to the invention comprise dimethyl sulfoxide as the at least one solvent b).

According to a further especially preferred embodiment, the formulations according to the invention comprise, as one solvent b), dimethyl sulfoxide and at least one second solvent b) which is other than dimethyl sulfoxide and which is preferably selected among hydroxylated ($C_5$-$C_8$)alkanecarboxylic esters, aliphatic ($C_5$-$C_8$)-di- and -triols, ($C_5$-$C_8$)-alkanecarboxylic acid alkoxyalkyl esters, ($C_3$-$C_4$)alkylene carbonates, γ-butyrolactone, N-methyl-($C_3$-$C_5$)-lactams and tri($C_1$-$C_3$)alkyl phosphates, in particular among γ-butyrolactone, methoxypropyl acetate, 2-methyl-2,4-pentanediol, hexylene glycol (1,6-hexanediol), tetrahydrofurfuryl alcohol and n-propyl lactate.

In a likewise preferred embodiment of the invention, the formulation comprises no or less than 0.1% by weight DMSO, based on the total weight of the formulation. In this embodiment of the invention, solvent b) is preferably selected among hydroxylated ($C_4$-$C_8$)-alkanecarboxylic esters, aliphatic ($C_5$-$C_8$)-di- and -triols, ($C_5$-$C_8$)-alkanecarboxylic alkoxyalkyl esters, tetrahydrofurfuryl alcohol, ($C_4$-$C_5$)-lactones and N-methyl-($C_4$-$C_5$)-lactams and in particular selected among γ-butyrolactone, dimethyl sulfoxide, methoxypropyl acetate, 2-methyl-2,4-pentanediol, hexylene glycol (1,6-hexanediol), tetrahydrofurfuryl alcohol and n-propyl lactate.

In general, the total amount of solvent b) which is present in the formulations of the invention depends on the amount of organic plant protectants a), surfactants e) and f) and solvents c) and d), and on their properties. The weight ratio of solvent b) and the total amount of plant protectants a) will usually be in the range of from 0.05:1 to 30:1, preferably in the range of from 0.1:1 to 10:1 and in particular in the range of from 0.15:1 to 5:1. Based on the total weight of the undiluted formulations, the amount of solvent b) is, as a rule, from 1 to 60% by weight, preferably from 10 to 40% by weight and in particular from 15 to 35% by weight. In the case of formulations which comprise DMSO as the only solvent b), the amount of DMSO is preferably not more than 5% by weight, for example from 1 to 5% by weight, based on the total weight of the formulation. In the case of formulations which comprise DMSO in combination with at least one further solvent (b), the weight ratio of DMSO to the further solvent b) is, as a rule, from 1:20 to 1:1, in particular in the range of from 1:10 to 1:2. In these formulations, the amount of DMSO is preferably no more than 5% by weight, for example 0.5 to 5% by weight, based on the total weight of the formulation.

The formulations according to the invention comprise at least one solvent c) with a water solubility of from 2 to 100 g/l, in particular 3 to 90 g/l or 4 to 80 g/l, at 20° C. Solvent c) can be selected from among a multiplicity of organic solvents with medium polarity. It is preferably selected among ($C_5$-$C_9$)-alkanecarboxylic alkyl esters, ($C_9$-$C_{12}$)-alkanecarboxylic alkoxyalkyl esters, ($C_5$-$C_9$)-dialkyldicarboxylic esters, ($C_5$-$C_9$)-ketones, ($C_5$-$C_9$)-arylalkyl alcohols, ($C_5$-$C_9$)-aryloxyalkyl alcohols, ($C_5$-$C_9$)-cycloalkyl alcohols, ($C_5$-$C_9$)-alkanediol alkoxides, ($C_5$-$C_9$)-alkanetriol alkoxides and ($C_5$-$C_6$)-alkylene carbonates.

In the present context, ($C_5$-$C_9$)-alkanecarboxylic alkyl esters are understood as meaning, in particular, alkanecarboxylic acids which are esterified with alkanols, where the total number of the carbon atoms is 5 to 9 and in particular 5, 6, 7 or 8. Examples are isopropyl acetate, n-propyl acetate, isobutyl acetate, tert-butyl acetate, n-pentyl acetate, cyclopentyl acetate, n-hexyl acetate, 3-methylcyclopentyl acetate, cyclohexyl acetate, n-heptyl acetate, 3-methylcyclohexyl acetate, n-propyl propionate, isopropyl propionate, n-butyl propionate, tert-butyl propionate, n-pentyl propionate, n-propyl isopropionate, cyclopropyl propionate, cyclopropyl isopropionate, isopropyl isopropionate, n-butyl isopropionate, tert-butyl isopropionate, n-pentyl isopropionate, n-hexyl propionate, cyclohexyl propionate, ethyl butyrate, n-propyl butyrate, isopropyl butyrate, n-butyl butyrate, tert-butyl butyrate, ethyl tert-butyrate, n-propyl tert-butyrate, isopropyl tert-butyrate, n-butyl tert-butyrate, tert-butyl tert-butyrate, n-pentyl butyrate, methyl pentanoate, ethyl pentanoate, propyl pentanoate, isopropyl pentanoate, n-butyl pentanoate, methyl hexanoate, ethyl hexanoate, isopropyl hexanoate, methyl heptanoate, ethyl heptanoate and methyl octanoate.

In the present context, ($C_9$-$C_{12}$)-alkanecarboxylic alkoxyalkyl ester is understood as meaning an ester of an alkanecarboxylic acid with an alkoxyalkanol, where the total number of carbon atoms is 9 to 12. Examples are isopropoxybutyl acetate, ethylene glycol propyl ether butyrate, ethylene glycol pentyl ether propionate, ethylene glycol 2-methylbutyl ether formate, propylene glycol ethyl ether pentanoate, propylene glycol butyl ether 2-methylpropylate, isopropoxypropyl butyrate, propoxypentyl tert-butyrate, ethoxypropyl butyrate, ethoxypropyl 2-ethylpropylate, ethylene glycol ethyl ether hexanoate, ethylene glycol propyl ether 3-methylpentanoate, ethoxymethyl heptanoate, ethoxybutyl hexanoate and methoxypropyl 3-ethylbutyrate.

In the present context, ($C_5$-$C_9$)-dialkyldicarboxylic esters is understood as meaning a diester of an alkanedicarboxylic acid with two alkanols which are selected independently of one another, where the total number of carbon atoms is 5 to 9 and in particular 5, 6, 7 or 8. Examples are ethyl methyl oxalate, diethyl oxalate, ethyl propyl oxalate, ethyl isopropyl oxalate, dipropyl oxalate, propyl isopropyl oxalate, ethyl butyl oxalate, methyl pentyl oxalate, propyl butyl oxalate, dimethyl malonate, methyl ethyl malonate, diethyl malonate, propyl ethyl malonate, isopropyl ethyl malonate, methyl propyl malonate, methyl isopropyl malonate, dipropyl malonate, dimethyl succinate, ethyl methyl succinate, diethyl succinate, methyl propyl succinate, methyl isopropyl succinate, ethyl propyl succinate, dimethyl glutarate, ethyl methyl glutarate, diethyl glutarate, dimethyl adipate, ethyl methyl adipate and dimethyl pimelate.

Within the scope of the present invention, the term "($C_5$-$C_9$)-ketones" comprises optionally alkoxylated aliphatic, cycloaliphatic and araliphatic ketones having 5 to 9 carbon atoms; these include, for example, 2-pentanone, 3-pentanone, 2-hexanone, 3-hexanone, 2-heptanone, 3-heptanone, 4-heptanone, 2-octanone, 3-octanone, 4-octanone, 4-methyl-2-pentanone, 5-methyl-2-hexanone, cyclopentanone, cyclohexanone, cycloheptanone, cyclooctanone, cyclohexylcarboxymethane, acetophenone and methoxyacetophenone.

A $(C_5-C_9)$-arylalkyl alcohol ($=(C_5-C_9)$-arylalkanol) is understood as meaning an alkanol which is substituted by an aryl radical, the $(C_5-C_9)$-arylalkyl alcohol comprising a total of 5 to 9 carbon atoms. Examples are benzyl alcohol, 2-phenylethanol, 1-phenylethanol, phenylpropanol, pyridin-1-ylmethanol, pyridin-3-ylmethanol, 1-pyridin-3-ylethanol, pyridinylbutanol, pyrimidin-1-ylmethanol, pyrimidin-1-ylethanol, 2-pyrimidin-3-ylpropanol, furan-2-ylmethanol, 2-furan-2-ylethanol, 3-furan-3-ylpropanol and 4-furan-2-ylbutanol.

A $(C_5-C_9)$-aryloxyalkyl alcohol ($=(C_5-C_9)$-aryloxyalkanol) is understood as meaning an alkanol which is substituted by an aryloxy radical, where the $(C_5-C_9)$-aryloxyalkyl alcohol comprises 5 to 9 carbon atoms. Examples are phenoxymethanol, phenoxyethanol and phenoxyisopropanol.

In the present context, $(C_5-C_9)$-cycloalkyl alcohols refer to cyclic alkanols having 5 to 9 carbon atoms such as, for example, cyclopentanol, cyclohexanol, cycloheptanol and cyclooctanol.

In the present context, a $(C_5-C_9)$-alkanediol alkanoate is understood as meaning an alkanediol which is esterified with two alkanoic acids, where the $(C_5-C_9)$-alkanediol alkoxide comprises 5 to 9 carbon atoms. Examples are diacetin, glycol diacetate, glycol dipropionate, glycerol dipropionate and propylene glycol diacetate.

In the present context, a $(C_5-C_9)$-alkanetriol alkanoate is understood as meaning an alkanetriol which is esterified with three alkanoic acids, where the $(C_5-C_9)$-alkanetriol alkoxide comprises 5 to 9 carbon atoms. An example is triacetin.

In the present context, $(C_5-C_6)$-alkylene carbonates refer to, in particular, cyclic diesters of carbonic acid having 5 to 6 carbon atoms, such as, for example, 1,2-butylene carbonate and 2,3-butylene carbonate.

According to a preferred embodiment, the formulations according to the invention comprise at least one solvent c) which is selected from $(C_5-C_9)$-ketones, $(C_5-C_9)$-arylalkyl alcohols, $(C_5-C_9)$-aryloxyalkyl alcohols, $(C_5-C_9)$-alkanetriol alkanoates and $(C_5-C_6)$-alkylene carbonates, and which is in particular selected from acetophenone, benzyl alcohol, cyclohexanone, 2-heptanone, triacetin, butylene carbonate and 2-phenoxyethanol.

The total amount of solvent c) which is present in the formulations of the invention generally depends on the amounts of organic plant protectants a), surfactants e) and f), and solvents b) and d), and their properties. The weight ratio of solvent c) and the total amount of plant protectants a) will generally be in the range of from 0.05:1 to 30:1, preferably in the range of from 0.1:1 to 20:1, and in particular in the range of from 0.5:1 to 10:1. Based on the total weight of the undiluted formulations, the amount of solvent c) is, as a rule, from 1 to 60% by weight, preferably from 10 to 40% by weight and in particular from 15 to 35% by weight.

The formulations according to the invention comprise at least one solvent d) with a water solubility of less than 2 g/l, preferably no more than 1 g/l and in particular no more than 0.5 g/l, at 20° C. Solvent d) can be selected from a multiplicity of unpolar solvents such as, for example, aliphatic or aromatic hydrocarbons, vegetable oils, fatty acids and their derivatives. The solvent d) is preferably selected among aliphatic, aromatic and cycloaliphatic hydrocarbons with boiling points of from 100 to 310° C., $(C_8-C_{20})$-alkylphenols, $(C_8-C_{20})$-alkanols, $(C_{10}-C_{20})$-alkanecarboxylic alkyl esters, $(C_9-C_{20})$-hydroxyalkanecarboxylic alkyl esters, $(C_{12}-C_{20})$-cycloalkanecarboxylic alkyl esters, $(C_{12}-C_{28})$-cycloalkanedicarboxylic dialkyl esters, $(C_{10}-C_{15})$-dialkyl dicarboxylates, $(C_{25}-C_{35})$-alkanetriol alkanoates, N—$(C_6-C_{18})$-alkyl-$(C_3-C_5)$-lactams, $(C_8-C_{26})$-fatty acids, in particular $C_{12}-C_{20}$-fatty acids, their dialkyl amides, e.g. their di-$C_1-C_4$-alkylamides such as the dimethyl amides, and their alkyl esters, e.g. their $C_1-C_8$-alkyl esters such as the methyl and ethyl esters.

In the present context, aliphatic hydrocarbons having boiling points of from 100 to 310° C., in particular from 120 to 280° C. (at atmospheric pressure), refer in particular to linear and branched alkanes or alkenes which have 7 to approximately 18 carbon atoms and which have a boiling point at atmospheric pressure in the above-mentioned range, in particular also mixtures of these aliphatic hydrocarbons. Such mixtures are commercially available for example under the trade name Exxsol, this being products which comprise mainly petroleum whose aromatic constituents have been depleted, such as, for example, Exxsol D30, Exxsol D40, Exxsol D80, Exxsol D100, Exxsol D120 and Exxsol D220/230.

Within the scope of the present invention, aromatic hydrocarbons having boiling points of from 100 to 310° C., in particular from 120 to 280° C. (at atmospheric pressure), are understood as meaning mono- and polycyclic aromatics which optionally have attached to them one or more aliphatic or aralipatic substituents, in particular alkyl or arylalkyl radicals and which have a boiling point at atmospheric pressure in the above-mentioned region. This is preferably understood as meaning mixtures of those aromatic hydrocarbons which are obtained as fractions in the distillation of, in particular, mineral oil products in the abovementioned boiling point range, such as the commercially available products which are known by the trade names Solvesso®, in particular Solvesso® 100, Solvesso® 150, Solvesso® 200, Solvesso® 150 ND, Solvesso® 200 ND, Aromatic®, in particular Aromatic® 150 and Aromatic® 200, Hydrosol®, in particular Hydrosol® A 200 und Hydrosol® A 230/270, Caromax®, in particular Caromax® 20 and Caromax® 28, Aromat K 150, Aromat K 200, Shellsol®, in particular Shellsol® A 100 und Shellsol® A 150, and Fin FAS-TX, in particular Fin FAS-TS 150 and Fin FAS-TX 200. Especially preferred are the mixtures Solvesso® 150 ND and Solvesso® 200 ND (ExxonMobil Chemical), in which the potential carcinogen naphthalene has been depleted. Thus, Solvesso® 150 ND comprises predominantly aromatic hydrocarbons which have 10 or 11 carbons, which boil in the range of from 175 to 209° C. and which are predominantly alkylbenzenes, while Solvesso® 200 ND comprises predominantly aromatic hydrocarbons which have 10 to 14 carbons, which boil in the range of from 235 to 305° C. and which are predominantly alkylnaphthalenes. A further example of the aromatic hydrocarbons mentioned here is a product available under the trade name Hisol SAS-296, which is a mixture of 1-phenyl-1-xylylethane and 1-phenyl-1-ethylphenylethane.

Within the scope of the present invention, cycloaliphatic hydrocarbons with boiling points of from 100 to 310° C., in particular from 120 to 280° C. (at atmospheric pressure), are understood as meaning saturated and unsaturated hydrocarbons which comprise a nonaromatic carbocycle, and mixtures of such hydrocarbons. An example is limonene.

The term $(C_8-C_{20})$-alkylphenol refers to a phenol which is substituted on the ring by at least one alkyl radical, with the $(C_8-C_{20})$-alkylphenol having 8 to 20 carbon atoms. Examples are ethylphenol, 2-methyl-4-ethylphenol, diheptylphenol and dodecylphenol.

In the present context, $(C_8-C_{20})$-alkanols are understood as meaning alkanols having 8 to 20 and in particular 8 to 14 carbon atoms ($=C_8-C_{14}$-alkanols). Examples are octanol, decanol, dodecanol, tridecanol, nonanol, isononanol, 2-propylheptanol, isotridecanol and ethylhexanol.

In the present context, ($C_{10}$-$C_{20}$)-alkanecarboxylic alkyl esters are understood as meaning, in particular, ($C_1$-$C_9$)-alkanecarboxylic acids which are esterified with alkanols, the total number of carbon atoms being 10 to 20. Examples are ethyl hexyl acetate, n-nonyl acetate, isobornyl acetate, propyl heptyl isopropionate, n-decyl butyrate, tert-butyl hexanoate, n-pentyl-4-ethyl octanoate and ethyl nonanoate.

In the present context, ($C_9$-$C_{20}$)-hydroxyalkanecarboxylic alkyl esters are understood as meaning, in particular, hydroxylated alkanecarboxylic acids which are esterified with alkanols, in particular esterified lactic acid (lactates), the total number of carbon atoms being 9 to 20. The alkyl radical frequently has from 3 to 10 carbon atoms. Examples are tert-butyl 3-hydroxydecanoate, n-propyl 4-hydroxyoctanoate, isopropyl hexyl 4-hydroxyoctanoate, ethyl 3-propyl-4-hydroxyhexanoate, n-pentyl 4-hydroxybutyrate, ethyl hexyl 3-hydroxybutyrate, 2-ethyl pentyl lactate, decyl lactate, ethyl hexyl lactate, n-heptyl hydroxyacetate, cyclohexyl ethyl hydroxyacetate and 3-isopropyl cyclopentyl hydroxyacetate.

In the present context, ($C_{12}$-$C_{28}$)-cycloalkanecarboxylic alkyl esters or ($C_{12}$-$C_{28}$)-cycloalkanedicarboxylic dialkyl esters are understood as meaning cycloalkanes which are substituted by one or two carboxyl groups, respectively, and which are esterified with one or two alkanols, respectively, the total number of the carbon atoms being 12 to 28. Examples are hexyl cyclopentanecarboxylate, pentyl cyclohexanecarboxylate, 3-isopropylhexyl cyclohexanecarboxylate, dibutyl 1,2-cyclopentanedicarboxylate, ethyl butyl 1,3-cyclopentanedicarboxylate, didecyl 1,2-cyclohexanedicarboxylate, methyl octyl 1,4-cyclohexanedicarboxylate and diisononyl cyclohexanedicarboxylate.

In the present context, ($C_{10}$-$C_{15}$)-dialkyldicarboxylates are understood as meaning a diester of an alkanedicarboxylic acid with two alkanols, where the total number of carbon atoms is 10 to 15. The alkyl radical frequently has in each case from 2 to 8 carbon atoms. Examples are butyl hexyl oxalate, dipentyl oxalate, diisobutyl malonate, dihexyl malonate, ethyl pentyl malonate, dipropyl succinate, diisopropyl succinate, diisobutyl succinate, dipentyl succinate, diisopropyl glutarate, diisobutyl glutarate, ethyl pentyl glutarate, dicyclopentyl glutarate, diisobutyl adipate, ethyl propyl adipate, diisobutyl pimelate and diethyl pimelate.

In the present context, ($C_{25}$-$C_{35}$)-alkanetriol alkanoates is understood as meaning an alkanetriol which is esterified with three alkanoic acids, where the ($C_{25}$-$C_{35}$)-alkanetriol alkanolate comprises 25 to 35 carbon atoms. An example is Myritol® 312 (Cognis), which is a mixture of triglycerides with ($C_8$-$C_{10}$)-fatty acid residues.

In the present context, N—($C_6$-$C_{18}$)-alkyl-($C_3$-$C_5$)-lactams are understood as meaning N-alkylated lactam derivatives having 3, 4 or 5 carbon atoms in the ring, where the N-alkyl radicals comprise 6 to 18 carbon atoms. An example is N-octylpyrrolidone.

In the present context, ($C_8$-$C_{26}$)-fatty acids are understood as meaning fatty acids with 8 to 26 carbon atoms. Examples are the saturated fatty acids caprylic acid, capric acid, lauric acid, myristic acid, palmitic acid, margaric acid, stearic acid, arachidic acid, behenic acid, lignoceric acid and cerotic acid; and the monounsaturated fatty acids undecenoic acid, palmitoleic acid, oleic acid, elaidic acid, vaccenic acid, icosenoic acid, cetoleic acid, erucic acid and nervonic acid; and the polyunsaturated fatty acids linoleic acid, α-linolenic acid, γ-linolenic acid, arachidonic acid, timnodonic acid, clupanodonic acid and cervonic acid. Examples of dialkylamides of the ($C_8$-$C_{26}$)-fatty acids are their di-$C_1$-$C_4$-alkylamides, e.g. the dimethylamides, diethylamides, dipropylamides, diisopropylamides, dibutylamides, diisobutylamides, methylethylamides, methylpropylamides, methylisobutylamides, methyl-tert-butylamides, ethylpropylamides, ethylisopropylamides, ethylbutylamides, ethylisobutylamides, propylisopropylamides, propylbutylamides and propylisobutylamides of the abovementioned fatty acids, the dimethyl amides being particularly preferred. Examples of alkyl esters of the ($C_8$-$C_{26}$)-fatty acids are their $C_1$-$C_8$-alkyl esters, e.g. the methyl esters, ethyl esters, propyl esters, isopropyl esters, butyl esters, isobutyl esters, tert-butyl esters, 1-methyl propyl esters, pentyl esters, 1-methyl butyl esters, 2-methyl butyl esters, 3-methyl butyl esters, hexyl esters, 1-methyl pentyl esters, 2-methyl pentyl esters, 1-ethyl butyl esters and 1,2-dimethyl butyl esters, heptyl esters, 1-methyl hexyl esters, 2-methyl hexyl esters, 3-methyl hexyl esters, 4-methyl hexyl esters, 5-methyl hexyl esters, 1-ethyl pentyl esters, 2-ethyl pentyl esters, 3-ethyl pentyl esters, 4-ethyl pentyl esters, 1,2-dimethyl pentyl esters, 1,3-dimethyl pentyl esters, 1,4-dimethyl pentyl esters, 2,3-dimethyl pentyl esters and ethyl-2-methyl butyl esters of the abovementioned fatty acids, the methyl and ethyl esters being particularly preferred.

According to a preferred embodiment, the formulations according to the invention comprise at least one solvent d) which is selected from among ($C_8$-$C_{26}$)-fatty acids, their di-$C_1$-$C_4$-alkylamides, for example the dimethyl amides, ($C_{10}$-$C_{15}$)-dialkyl-dicarboxylic esters, alkyl esters of ($C_9$-$C_{20}$)-hydroxyalkanecarboxylic acids, in particular lactates with a total of 9 to 20 C atoms, and aromatic hydrocarbons with a boiling point at atmospheric pressure in the range of from 100 to 310° C. According to a very preferred embodiment, the formulations according to the invention comprise at least one solvent d) which is selected from a group consisting of $C_{12}$-$C_{20}$-fatty acids, e.g. the commercial product Edenor® TI 05 (Cognis), which is, according to the manufacturer, a fatty acid mixture with a high oleic acid content, dimethyl amides of $C_{12}$-$C_{20}$-fatty acids, e.g. the commercial product Agnique® KE 3658, (Cognis), which is a mixture of fatty acid dimethylamides, ($C_8$-$C_{14}$)-alkanols, e.g. dodecanol, aromatic hydrocarbons having a boiling point at atmospheric pressure in the range from 120 to 280° C., e.g. Solvesso® 150 ND and Solvesso® 200 ND, and comparable products, $C_6$-$C_{10}$-alkyl lactates with a total of 9 to 13 C atoms such as 2-ethylhexyl lactate, and diisobutyl dicarboxylates with a total of 10 to 15 C atoms, for example technical-grade mixtures of diisobutyl esters of succinic acid, glutaric acid and adipic acid.

The total amount of solvent d) which is present in the formulations of the invention generally depends on the amount of organic plant protectants a), surfactants e) and f) and solvents b) and c), and on their properties. The weight ratio of solvent d) and the total amount of plant protectants a) will generally be in the range of from 0.05:1 to 30:1, preferably in the range of from 0.1:1 to 20:1 and in particular in the range of from 0.5:1 to 15:1. Based on the total weight of the undiluted formulations, the amount of solvent d) is, as a rule, from 1 to 60% by weight, preferably from 5 to 45% by weight and in particular from 10 to 35% by weight.

In a preferred embodiment, the formulations according to the invention comprise in each case only one solvent b), c) and d); and according to a further preferred embodiment, they additionally comprise only one further solvent b) or c).

The formulations according to the invention comprise at least one nonionic surfactant e) and at least one anionic surfactant f). The term surfactant refers to surface-active substances, hereinbelow also termed emulsifiers or detergents.

The purpose of the surfactant mixture is to reduce the surface tension between the continuous and the disperse phase and thereby to stabilize the particles/droplets of the disperse phase. The surfactants also help to solubilize the at least one organic plant protectant a). The skilled worker is familiar with suitable surfactants for formulating microemulsions, for example through McCutcheon, Detergents and Emulsifiers, Int. Ed., Ridgewood, N.Y. The surfactants may be polymeric or nonpolymeric surfactants. Preferably, the predominant portion, in particular at least 90% and specifically all of the surfactant present in the microemulsion, is selected from the group of the nonpolymeric surfactants, which are also referred to as emulsifiers. Usually, nonpolymeric surfactants (emulsifiers) have an average molecular weight (number average) of up to 2000 Daltons, in particular form 150 to 2000 Daltons and preferably from 200 to 1500 Daltons.

The group of the nonionic surfactants comprises in particular:

homo- or cooligomers of the $(C_2-C_4)$-alkylene oxides, such as ethylene oxide, propylene oxide (=1-methyloxirane), 1,2-butylene oxide (=1-ethyloxirane) and 2-methylpropylene oxide (=1,1-dimethyloxirane), in particular homooligomers of ethylene oxide, homooligomers of propylene oxide and ethylene oxide/propylene oxide cooligomers;

oligo-$(C_2-C_4)$-alkylene oxide $(C_8-C_{22})$-alkyl ethers, in particular oligoethoxylates and oligoethoxylate-co-propoxylates of the linear and branched $(C_8-C_{22})$-alkanols, preferably oligoethoxylates of the fatty alcohols and oligoethoxylates of the oxo alcohols, such as, for example, lauryl alcohol oligoethoxylate, isotridecanol oligoethoxylate, cetyl alcohol oligoethoxylate, stearyl alcohol oligoethoxylate and their esters, such as, for example, the acetates;

oligo-$(C_2-C_4)$-alkylene oxide aryl ethers and oligo-$(C_2-C_4)$-alkylene oxide $(C_1-C_{16})$-alkylaryl ethers, such as, for example, oligo-$(C_2-C_4)$-alkylene oxide $(C_1-C_{22})$-alkylbenzene ethers, in particular oligoethoxylates of the $(C_1-C_{16})$-alkylphenols such as, for example, the oligoethoxylate of nonylphenol, decylphenol, isodecylphenol, dodecylphenol or isotridecylphenol;

oligo-$(C_2-C_4)$-alkylene oxide mono-, -di- or -tristyrylphenyl ethers, in particular oligoethoxylates of the mono-, di- and tristyrylphenols, and their condensates with formaldehyde and their esters, such as, for example, the acetates;

$(C_6-C_{22})$-alkylglucosides and $(C_6-C_{22})$-alkyloligoglucosides;

oligoethoxylates of the $(C_6-C_{22})$-alkylglucosides and oligoethoxylates of the $(C_6-C_{22})$-alkyloligoglucosides;

oligoethoxylates of the fatty acids and oligoethoxylates of the hydroxyl fatty acids;

partial esters of polyols with $(C_6-C_{22})$-alkanoic acids, in particular mono- and diesters of glycerol and mono-, di- and triesters of sorbitan, such as, for example, glycerol monostearate, sorbitan monododecanoate, sorbitan dioleate and sorbitan tristearate;

oligoethoxylates of the partial esters of polyols with $(C_6-C_{22})$-alkanoic acids, in particular oligoethoxylates of the mono- and diesters of glycerol and oligoethoxylates of the mono-, di- and triesters of sorbitan, such as, for example, oligoethoxylates of glycerol monostearate, oligoethoxylates of sorbitan monooleate, oligoethoxylates of sorbitan monostearate and oligoethoxylates of sorbitan tristearate;

oligoethoxylates of vegetable oils or animal fats, such as, for example, corn oil ethoxylate, castor oil ethoxylate, tall oil ethoxylate; acetylene glycols such as, for example, 2,4,7,9-tetramethyl-4,7-dihydroxy-5-decine;

oligooxyethylene/oligooxypropylene block cooligomers; and oligoethoxylates of fatty amines or of fatty acid diethanolamides.

The term oligo-$(C_2-C_4)$-alkylene oxide ether or oligo-$(C_2-C_4)$-alkylene oxide refers to oligoether radicals which are derived from $(C_2-C_4)$-alkylene oxides such as ethylene oxide, propylene oxide (=1-methyloxirane), 1,2-butylene oxide (=1-ethyloxirane) and 2-methylpropylene oxide (=1,1-dimethyloxirane). Accordingly, the term oligo-$(C_2-C_3)$-alkylene oxide ether refers to oligoether radicals which are derived from $(C_2-C_3)$-alkylene oxides such as ethylene oxide and propylene oxide. The term ethoxylate refers to oligoether radicals which are derived from ethylene oxide. Analogously, the term oligoethylene oxide co-oligopropylene oxide refers to polyether radicals which are derived from mixtures of ethylene oxide and propylene oxide. The number of repeating units in the oligoether radicals is generally between 2 and 120, frequently between 4 and 80, and in particular between 5 and 60.

Among the abovementioned nonionic surfactants, the following are preferred:

homo- or cooligomers of the $(C_2-C_3)$-alkylene oxides, oligo-$(C_2-C_4)$-alkylene oxide $(C_8-C_{22})$-alkyl ethers, oligo-$(C_2-C_4)$-alkylene oxide $(C_1-C_{16})$-alkylbenzene ethers, oligo-$(C_2-C_4)$-alkylene oxide mono-, -di- or -tristyrylphenyl ethers, oligo-$(C_2-C_4)$-alkylene oxide mono- or -distyrylphenyl ether/formaldehyde condensates, partial esters of glycerol or sorbitan with fatty acids, and acetylene glycols, and mixtures thereof.

Nonionic surfactants which are especially preferred within the scope of the present invention include oligo-$(C_2-C_3)$-alkylene oxide $(C_8-C_{22})$-alkyl ethers, homo- or cooligomers of the $(C_2-C_3)$-alkylene oxides and oligo-$(C_2-C_3)$-alkylene oxide mono-, -di- or -tristyrylphenyl ethers, and mixtures thereof.

In a preferred embodiment of the invention, component e) of the formulations comprises at least two nonionic surfactants with different HLB values. According to an especially preferred embodiment, the at least two nonionic surfactants are:

e.1) at least one surfactant with an HLB value of no more than 13, in particular of 5 to 13 and specifically of 6 to 12; and e.2) at least one surfactant with an HLB value of over 13, in particular of 13.5 to 18 and specifically of 14 to 17.

In the context of the present invention, the term "HLB value" ("hydrophilic-lipophilic balance") is a measure for the degree of hydrophilicity or lipophilicity of a surfactant. The HLB value can be used for predicting the surfactant properties of a molecule. According to the method of Davies (Davies, J. T., Proceedings of the International Congress of Surface Activity, 1957, 426-438), this value is calculated using the following formula:

$$HLB = 7 + m*H^h + n*H^l$$

where m represents the number of hydrophilic groups of the molecule, $H^h$ is a value which corresponds to the specific hydrophilic character of the hydrophilic groups, n represents the number of lipophilic groups of the molecule and $H^l$ is a value which corresponds to the specific hydrophilic character of the lipophilic groups.

The nonionic surfactant e.1) with an HLB value of no more than 13 may be selected from among all abovementioned nonionic surfactants which have an HLB value of no more than 13, in particular from 5 to 13 or from 6 to 12. Suitable surfactants e.1) comprise, in particular, oligo-$(C_2-C_4)$-alkylene oxide $(C_8-C_{22})$-alkyl ethers, oligo-$(C_2-C_4)$-alkylene oxide $(C_8-C_{22})$-alkylbenzene ethers, mono fatty acid esters of sorbitan and oligo-$(C_2-C_4)$-alkylene oxide mono-, -di- or -tristyrylphenyl ethers. The at least one nonionic surfactant e.1) is preferably an oligo-$(C_2-C_4)$-alkylene oxide $(C_8-C_{22})$-alkyl ether, in particular an oligo-$(C_2-C_4)$-alkylene oxide $(C_8-C_{22})$-alkyl ether with an HLB value in the range of from 4 to 12. Nonionic surfactants e.1) which are especially preferred are those selected from among oligoethoxides and oligoethoxylate co-propoxides of linear or branched $(C_8-C_{22})$-alkanols. Examples of such preferred surfactants are ethoxides of branched $C_{13}$-alcohols which are commercially available under the trade names Lutensol® TO3, Lutensol® TO5 and Lutensol® TO7.

The nonionic surfactant e.2) with an HLB value of over 13 can be selected from among all abovementioned nonionic surfactants which have an HLB value of over 13, in particular from 13.5 to 18 or from 14 to 17. Suitable surfactants e.2) comprise, in particular, homo- and cooligomers of the $(C_2-C_3)$-alkylene oxides, oligo-$(C_2-C_3)$-alkylene oxide $(C_8-C_{22})$-alkyl ethers, oligo-$(C_2-C_3)$-alkylene oxide $(C_8-C_{22})$-alkylbenzene ethers and oligo-$(C_2-C_3)$-alkylene oxide mono-, -di- or -tristyrylphenyl ethers. Preferably, the at least one nonionic surfactant e.2) is selected among homo- and cooligomers of the $(C_2-C_3)$-alkylene oxides and oligo-$(C_2-C_3)$-alkylene oxide mono-, -di- or -tristyrylphenyl ethers, in particular among homo- and copolymers of the $(C_2-C_3)$-alkylene oxides and oligo-$(C_2-C_3)$-alkylene oxide mono-, -di- and -tristyrylphenyl ethers with HLB values in the range of from 13.5 to 18, in particular from 14 to 17. Especially preferred surfactants e.2) are those selected from among propylene oxide/ethylene oxide block cooligomers and oligoethylene oxide tristyrylphenyl ethers. Examples of such preferred surfactants are ethoxides of tristyrylphenol which are commercially available under the trade name Soprophor®, in particular Soprophor® S 25 and Soprophor® S 40, or propylene oxide/ethylene oxide block cooligomers which are commercially available under the trade names Pluronic® PE, in particular Pluronic® PE 6200 and Pluronic® 6400, or ethoxides of branched $C_{13}$-alcohols which are commercially available under the trade names Lutensol® TO15.

Anionic surfactants f) comprise, in particular, the sodium, potassium, calcium and ammonium salts of
- $(C_6-C_{22})$-alkylsulfonates, such as, for example, laurylsulfonate and isotridecylsulfonate;
- $(C_6-C_{22})$-alkyl sulfates such as, for example, lauryl sulfate, isotridecyl sulfate, cetyl sulfate and stearyl sulfate;
- arylsulfonates, in particular $(C_1-C_{16})$-alkylbenzenesulfonates, such as, for example, cumylsulfonate, octylbenzenesulfonate, nonylbenzenesulfonate and dodecylbenzenesulfonate, naphthylsulfonate, mono- and di-$(C_1-C_{16})$-alkylnaphthylsulfonates, such as, for example, dibutylnaphthylsulfonate;
- mono- and di-$(C_1-C_{16})$-alkyldiphenyl ether (di)sulfonates, such as, for example, dodecyldiphenyl ether disulfonate;
- sulfates and sulfonates of fatty acids and fatty acid esters;
- oligo-$(C_2-C_3)$-alkylene oxide $(C_8-C_{22})$-alkyl ether sulfates, in particular sulfates of the ethoxides of $(C_8-C_{22})$-alkanols, such as, for example, sulfates of the ethoxides of lauryl alcohol;
- oligo-$(C_2-C_3)$-alkylene oxide $(C_1-C_{16})$-alkylbenzene ether sulfates, in particular sulfates of the ethoxylates of $(C_1-C_{16})$-alkylphenols;
- di-$(C_4-C_{18})$-alkyl esters of sulfosuccinic acids (=$(C_4-C_{18})$-dialkylsulfosuccinates), such as, for example dioctylsulfosuccinate;
- condensates of naphthalenesulfonic acid, $(C_1-C_{16})$-alkylnaphthalenesulfonic acid or phenolsulfonic acid with formaldehyde (=$(C_1-C_{16})$-naphthalenesulfonate/formaldehyde condensates, $(C_1-C_{16})$-alkylnaphthalenesulfonate/formaldehyde condensates and phenolsulfonate/formaldehyde condensates);
- oligo-$(C_2-C_3)$-alkylene oxide mono-, -di- and -tristyrylphenyl ether sulfates, in particular oligoethoxides of mono-, di- and tristyrylphenol;
- mono- and di-$(C_8-C_{22})$-alkyl sulfates;
- oligo-$(C_2-C_3)$-alkylene oxide $(C_8-C_{22})$-alkyl ether phosphates;
- oligo-$(C_2-C_3)$-alkylene oxide $(C_1-C_{16})$-alkylbenzene ether phosphates;
- oligo-$(C_2-C_3)$-alkylene oxide mono-, -di- and -tristyrylphenylether phosphates;
- oligoethylene oxide polycarboxylates, in particular homo- and cooligomers of monoethylenically unsaturated mono- or dicarboxylic acids having from 3 to 8 carbon atoms, where the cooligomers additionally have oligoethylene oxide side chains;
- fatty acids, such as, for example, stearic acid; and
- oligophosphates, such as, for example, hexametaphosphates and triphosphates (or tripolyphosphates).

Among the abovementioned anionic surfactants, the sodium, potassium, calcium and ammonium salts of the following are preferred:
- $(C_1-C_{16})$-alkylbenzenesulfonates;
- $(C_1-C_{16})$-alkylnaphthalenesulfonates;
- naphthalenesulfonate/formaldehyde condensates and $(C_1-C_{16})$-alkylnaphthalene-sulfonate/formaldehyde condensates;
- oligo-$(C_2-C_3)$-alkylene oxide $(C_8-C_{22})$-alkyl ether sulfates;
- oligo-$(C_2-C_3)$-alkylene oxide $(C_8-C_{22})$-alkyl ether phosphates;
- oligo-$(C_2-C_3)$-alkylene oxide $(C_1-C_{16})$-alkylbenzene ether sulfates;
- oligo-$(C_2-C_3)$-alkylene oxide $(C_1-C_{16})$-alkylbenzene ether phosphates;
- $(C_8-C_{22})$-alkyl sulfates,
- $(C_4-C_{18})$-dialkylsulfosuccinates,
- oligo-$(C_2-C_3)$-alkylene oxide mono-, -di- and -tristyrylphenyl ether sulfates;
- oligo-$(C_2-C_3)$-alkylene oxide mono-, -di- and -tristyrylphenyl ether phosphates,
- oligoethylene oxide polycarboxylates and
- polyphosphates, and mixtures of these.

Especially preferred anionic surfactants f) comprise the salts, in particular the sodium, potassium, calcium and ammonium salts of the oligo-$(C_2-C_3)$-alkylene oxide mono-, -di- and -tristyrylphenyl ether sulfates.

The weight ratio of anionic surfactants f) and nonionic surfactants e) of the surfactant mixtures in the formulations according to the invention is preferably in the range of from 0.05:1 to 10:1 and especially preferably in the range of from 0.1:1 to 4:1.

According to an especially preferred embodiment, component e) takes the form of two nonionic surfactants with different HLB values, in particular one surfactant e.1) and one surfactant e.2), and component f) takes the form of an anionic surfactant.

In general, the total amount of surfactant present in the formulations of the invention depends on the amount of organic plant protectants a) and of solvents b), c) and d) and their properties. The weight ratio of the total amount of surfactants e) and f) to the total amount of plant protectants a) will generally be in the range of from 0.3:1 to 30:1, preferably in the range of from 0.5:1 to 20:1 and in particular in the range of from 1:1 to 7:1. Based on the total weight of the undiluted formulations, the amount of surfactant is, as a rule, from 1 to 35% by weight, preferably from 5 to 25% by weight, and in particular from 10 to 25% by weight.

Based on the total weight of the undiluted formulations, the amount of nonionic surfactants e) is, as a rule, from 0.5 to 30% by weight, preferably from 4 to 24% by weight and in particular from 5 to 20% by weight.

Based on the total weight of the undiluted formulations, the amount of anionic surfactants d) is, as a rule, from 0.5 to 25% by weight, preferably from 1 to 20% by weight and in particular from 5 to 15% by weight.

The total amount of surfactants e) and f) and solvents b), c) and d) (=Organic solvents) which is present in the formulations of the invention generally depends on the nature and the amount of the organic plant protectants a). The weight ratio of surfactants e)+f) plus organic solvents b)+c)+d) to plant protectants a) will generally be in the range of from 75:1 to 0.5:1, preferably in the range of from 50:1 to 1:1, and in particular in the range of from 30:1 to 2:1. Based on the total weight of the undiluted formulations, the amount of surfactant plus solvents is, as a rule, from 10 to 95% by weight, preferably from 20 to 85% by weight and in particular from 40 to 75% by weight.

According to the invention, the active substance compositions comprise at least one organic plant protectant. In the present context, the term "plant protectant" is to be understood in the wide sense and comprises not only substances which protect plants from attack by harmful organisms, substances which destroy plant-damaging organisms or substances which prevent their development, but also substances which influence the growth of the useful plant, i.e. which enhance or reduce its growth, including substances which serve to improve plant health. Examples of the plant protectants include:

fungicides, i.e. active substances which destroy phytopathogenic fungi or reduce their growth or which reduce the infection of the useful plant by such phytopathogenic fungi;

insecticides, acaricides and nematicides, i.e. active substances which destroy phytopathogenic arthropods or nematodes or reduce their development in such a way that infection of the useful plant is effectively prevented or the infection of a plant by these harmful organisms is reduced;

herbicides, i.e. active substances which destroy a harmful plant or reduce or prevent its growth;

growth regulators, i.e. active substances which promote or reduce plant growth;

safeners, i.e. active substances which reduce or prevent a phytotoxic effect on the useful plants, caused by the abovementioned substances; and fertilizers.

The organic plant protectant is preferably a low-molecular weight organic plant protectant, i.e. a low-molecular-weight organic compound with a molecular weight in the range of from 150 to 500 Daltons.

Preferably, the plant protectant is solid at room temperature or a nonvolatile oil, i.e. it has a vapor pressure of less than 0.1 mbar at 25° C.

Preferably, the plant protectant has a solubility of at least 1 g/l, in particular at least 10 g/l, in the solvent b) or in the mixture of solvents b), c) and d) at 25° C.

Examples of suitable plant protectants are known for example from W. Krämer and U. Schirmer (Eds.) "Modern Crop Protection Compounds" Vol. 2, Wiley-VHC 2007; C. D. S. Tomlin, "The Pesticide Manual", 13th Edition, British Crop Protection Council (2003); and from "The Compendium of Pesticide Common Names", http://www.alanwood.net/pesticides/.

Examples of active substances with fungicidal activity are mentioned hereinbelow in groups A.1 to A.6:

A.1. Strobilurins such as, for example, azoxystrobin, dimoxystrobin, enestroburin, fluoxastrobin, kresoxim-methyl, metominostrobin, picoxystrobin, pyraclostrobin, trifloxystrobin, orysastrobin, methyl-(2-chloro-5-[1-(3-methylbenzyloxyimino)-ethyl]benzyl)carbamate, methyl-(2-chloro-5-[1-(6-methylpyridin-2-ylmethoxy-imino)ethyl]benzyl)carbamate, methyl 2-(ortho-((2,5-dimethylphenyloxy-methylene)phenyl)-3-methoxyacrylate;

A.2 Carboxamides such as, for example,

Carboxanilides: benalaxyl, benalaxyl-M, benodanil, carboxin, mebenil, mepronil, fenfuram, fenhexamid, flutolanil, furalaxyl, furcarbanil, furametpyr, metalaxyl, metalaxyl-M (mefenoxam), methfuroxam, metsulfovax, ofurace, oxadixyl, oxycarboxin, penthiopyrad, pyracarbolid, salicylanilide, tecloftalam, thifluzamide, tiadinil, N-2-cyanophenyl-3,4-dichloroisothiazol-5-carboxamide (isotianil);

N-Biphenylamides: bixafen, boscalid, N-(4'-bromobiphenyl-2-yl)-4-difluoromethyl-2-methylthiazol-5-carboxamide, N-(4'-trifluoromethylbiphenyl-2-yl)-4-difluoromethyl-2-methylthiazol-5-carboxamide, N-(4'-chloro-3'-fluorobiphenyl-2-yl)-4-difluoromethyl-2-methylthiazol-5-carboxamide, N-(3',4'-dichloro-4-fluorobiphenyl-2-yl)-3-difluoromethyl-1-methylpyrazole-4-carboxamide, N-(3',4',5'-trifluorobiphenyl-2-yl)-3-difluoromethyl-1-methylpyrazole-4-carboxamide;

Carboxylic acid morpholides: dimethomorph, flumorph;

Benzamides: flumetover, fluopicolid (picobenzamid), zoxamid;

Other carboxamides: carpropamid, diclocymet, mandipropamid, silthiofam, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide;

A.3. Azoles such as, for example,

Triazoles: bitertanol, bromuconazole, cyproconazole, difenoconazole, diniconazole, enilconazole, epoxiconazole, fenbuconazole, flusilazol, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;

Imidazoles: cyazofamid, imazalil, pefurazoate, prochloraz, triflumizole;

Benzimidazoles: benomyl, carbendazim, fuberidazole, thiabendazole;

Others: ethaboxam, etridiazole, hymexazol;

A.4. Nitrogen-containing heterocyclyl compounds such as, for example,

Pyridines: fuazinam, pyrifenox, 3-[5-(4-chlorophenyl)-2,3-dimethylisoxazolidin-3-yl]-pyridine;

Pyrimidines: bupirimate, cyprodinil, ferimzone, fenarimol, mepanipyrim, nuarimol, pyrimethanil;
piperazines: triforine;
Pyrroles: fludioxonil, fenpiclonil;
Morpholines: aldimorph, dodemorph, fenpropimorph, tridemorph;
Dicarboximides: iprodione, procymidone, vinclozolin;
Others: acibenzolar-S-methyl, anilazine, captan, captafol, dazomet, diclomezin, fenoxanil, folpet, fenpropidin, famoxadon, fenamidon, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;

A.5. Carbamates and dithiocarbamates such as, for example,
Dithiocarbamates: ferbam, mancozeb, maneb, metiram, metam, propineb, thiram, zineb, ziram;
Carbamates: diethofencarb, flubenthiavalicarb, iprovalicarb, propamocarb, methyl 3-(4-chlorophenyl)-3-(2-isopropoxycarbonylamino-3-methylbutyryl-amino)propionate, 4-fluorophenyl N-(1-(1-(4-cyanophenyl)ethanesulfonyl)but-2-yl)carbamate;

A.6. Other fungicides such as, for example,
Guanidines: dodine, iminoctadine, guazatine;
Antibiotics: kasugamycin, polyoxins, streptomycin, validamycin A;
Organometal compounds: fentin salts;
Sulfur-containing heterocyclyl compounds: isoprothiolane, dithianone;
Organophosphorous compounds: edifenphos, fosetyl, fosetyl-aluminum, iprobenfos, pyrazophos or tolclofos-methyl;
Organochlorine compounds: thiophanate-methyl, chlorothalonil, dichlofluanid, tolylfluanid, flusulfamide, phthalide, hexachlorobenzene, pencycuron, quintozene;
Nitrophenyl derivatives: binapacryl, dinocap, dinobuton;
Others: spiroxamine, cyflufenamid, cymoxanil, metrafenon.

Examples of active substances with insecticidal, acaricidal, and/or nematicidal activity are mentioned in groups B.1 to B.24:

B.1. Organo(thio)phosphates: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos (DDVP), dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, methyl-parathion, mevinphos, monocrotophos, naled, omethoate, oxydemeton-methyl, paraoxon, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, sulprophos, tebupirimfos, temephos, terbufos, tetrachlorvinphos, thiometon, triazophos, trichlorfon, vamidothion;

B.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

B.3. Pyrethroids: acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

B.4. Juvenile hormone mimetics: hydroprene, kinopren, methopren, fenoxycarb, pyriproxyfen;

B.5. Nicotin receptor agonist/antagonist compounds: acetamiprid, bensultap, cartap-hydrochloride, clothianidin, dinotefuran, imidacloprid, thiamethoxam, nitenpyram, nicotine, spinosad (allosteric agonist), spinetoram, thiacloprid, thiocyclam, thiosultap-sodium and AKD1022.

B.6. GABA-controlled chloride channel antagonist compounds: chlordan, endosulfan, gamma-HCH (lindan); acetoprole, ethiprole, fipronil, pyrafluprole, pyriprole, vaniliprole;

B.7. Chloride channel activators: abamectin, emamectin-benzoate, milbemectin, lepimectin;

B.8. METI I compounds: fenazaquin, fenpyroximate, pyrimidifen, pyridaben, tebufenpyrad, tolfenpyrad, flufenerim, rotenone;

B.9. METI II and III compounds: acequinocyl, fluacyprim, hydramethylnon;

B.10. Oxidative phosphorylation uncouplers: chlorfenapyr, DNOC;

B.11. Oxidative phosphorylation inhibitors: azocyclotin, cyhexatin, diafenthiuron, fenbutatin oxide, propargit, tetradifon;

B.12. Molting inhibitors: cyromazin, chromafenozide, halofenozide, methoxyfenozide, tebufenozide;

B.13. Synergists: piperonyl butoxide, tribufos;

B.14. Sodium channel blockers: indoxacarb, metaflumizon;

B.15. Selective antifeedants: crylotie, pymetrozine, flonicamid;

B.16. Mite growth inhibitors: clofentezine, hexythiazox, etoxazole;

B.17. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

B.18. Lipid biosynthesis inhibitors: spirodiclofen, spiromesifen, spirotetramate;

B.19. Octapaminergic agonists: amitraz;

B.20. Ryanodine receptor modulators: flubendiamide, (R)- and (S)-3-chloro-N1-{2-methyl-4-[1,2,2,2-tetrafluoro-1-(trifluoromethyl)ethyl]phenyl}-N2-(1-methyl-2-methylsulfonylethyl)phthalamide;

B.21. Others: amidoflumet, benclothiaz, benzoximate, bifenazate, bromopropylate, cyenopyrafen, cyflumetofen, quinomethionate, dicofol, fluoroacetate, phosphine, pyridalyl, pyrifluquinazone, organic sulfur compounds, sulfoxaflor, 4-but-2-ynyloxy-6-(3,5-dimethyl-piperidin-1-yl)-2-fluoropyrimidine, 3-benzoylamino-N-[2,6-dimethyl-4-(1,2,2,2-tetrafluoro-1-trifluoromethylethyl)-phenyl]-2-fluorobenzamide, 4-[5-(3,5-dichlorophenyl)-5-trifluoromethyl-4,5-dihydroisoxazol-3-yl]-2-methyl-N-pyridin-2-ylmethylbenzamide, 4-[5-(3,5-dichlorophenyl)-5-trifluoromethyl-4,5-dihydroisoxazol-3-yl]-2-methyl-N-(2,2,2-trifluoroethyl)benzamide, 4-[5-(3,5-dichlorophenyl)-5-trifluoromethyl-4,5-dihydro-isoxazol- 3-yl]-2-methyl-N-thiazol-2-ylmethylbenzamide (M22.5), 4-[5-(3,5-dichlorophenyl)-5-trifluoromethyl-4,5-dihydroisoxazol-3-yl]-2-methyl-N-(tetrahydrofuran-2-ylmethyl)benzamide, 4-{[(6-bromopyrid-3-yl)methyl](2-fluoroethyl)amino}furan-2(5H)-one, 4-{[(6-fluoropyrid-3-yl)methyl](2,2-difluoroethyl)amino}furan-2(5H)-one, 4-{[(2-chloro-1,3-thiazolo-5-yl)methyl](2-fluoroethyl)amino}furan-2(5H)-one, 4-{[(6-chloropyrid-3-yl)methyl](2-fluoroethyl)amino}furan-2(5H)-one, 4-{[(6-chloropyrid-3-yl)methyl](2,2-difluoroethyl)amino}furan-2(5H)-one, 4-{[(6-chloro-5-fluoropyrid-3-yl)methyl](methyl)amino}furan-2(5H)-one, 4-{[(5,6-dichloropyrid-3-yl)methyl](2-fluoroethyl)amino}furan-2(5H)-one, 4-{[(6-chloro-5-fluoropyrid-3-yl)methyl](cyclopropyl)amino}furan-2(5H)-one, 4-{[(6-chloropyrid-3-yl)methyl](cyclopropyl)amino}furan-2(5H)-one, 4-{[(6-chloropyrid-3-yl)methyl](methyl)amino}furan-2(5H)-one, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H, 11H-naphtho[2,1-b]pyrano[3,4-e]pyran-3,6-diyl]cyclopropane acetate, 8-(2-cyclopropylmethoxy-4-methyl-phenoxy)-3-(6-methyl-pyridazin-3-yl)-3-aza-bicyclo[3.2.1]octane (M22.18);

B.22. N—R'-2,2-dihalo-1-R"-cyclopropanecarboxamide-2-(2,6-dichloro-α,α,α-trifluoro-p-tolyl)hydrazone or N—R'-2,2-di-R'''-propionamid-2-(2,6-dichloro-α,α,α-trifluoro-p-tolyl)-hydrazone, in which R' represents methyl or ethyl, halo represents chloro or bromo, R" represents hydrogen or methyl and R''' represents methyl or ethyl;

B.23. Anthranilamide compounds: chloranthraniliprole, cyantraniliprole, N-[4-cyano-2-(1-cyclopropylethylcarbamoyl)-6-methyl-phenyl]-5-bromo-2-(3-chloropyridin-2-yl)-2H-pyrazole-3-carboxamide, N-[2-chloro-4-cyano-6-(1-cyclopropylethylcarbamoyl)phenyl]-5-bromo-2-(3-chloropyridin-2-yl)-2H-pyrazole-3-carboxamide, N-[2-bromo-4-cyano-6-(1-cyclopropylethylcarbamoyl)phenyl]-5-bromo-2-(3-chloropyridin-2-yl)-2H-pyrazole-3-carboxamide, N-[2-bromo-4-chloro-6-(1-cyclopropylethylcarbamoyl)phenyl]-5-bromo-2-(3-chloropyridin-2-yl)-2H-pyrazole-3-carboxamide, N-[2,4-dichloro-6-(1-cyclopropylethylcarbamoyl)phenyl]-5-bromo-2-(3-chloropyridin-2-yl)-2H-pyrazole-3-carboxamide, N-[4-chloro-2-(1-cyclopropylethylcarbamoyl)-6-methyl-phenyl]-5-bromo-2-(3-chloropyridin-2-yl)-2H-pyrazole-3-carboxamide, B.24. Malononitrile compounds: $CF_2HCF_2CF_2CF_2CH_2C(CN)_2CH_2CH_2CF_3$ (2-(2,2,3,3,4,4,5,5-octafluoropentyl)-2-(3,3,3-trifluoropropyl)malonitrile), $CF_3(CH_2)_2C(CN)_2CH_2(CF_2)_5CF_2H$ (2-(2,2,3,3,4,4,5,5,6,6,7,7-dodecafluoroheptyl)-2-(3,3,3-trifluoropropyl)malonitrile), $CF_3(CH_2)_2C(CN)_2(CH_2)_2C(CF_3)_2F$ (2-(3,4,4,4-tetrafluoro-3-trifluoromethylbutyl)-2-(3,3,3-trifluoropropyl)malonitrile), $CF_3(CH_2)_2C(CN)_2(CH_2)_2(CF_2)_3CF_3$ (2-(3,3,4,4,5,5,6,6,6-nonafluoro-hexyl)-2-(3,3,3-trifluoropropyl)malonitrile), $CF_2H(CF_2)_3CH_2C(CN)_2CH_2(CF_2)_3CF_2H$ (2,2-bis-(2,2,3,3,4,4,5,5-octafluoropentyl)malonitrile), $CF_3(CH_2)_2C(CN)_2CH_2(CF_2)_3CF_3$ (2-(2,2,3,3,4,4,5,5,5-nonafluoropentyl)-2-(3,3,3-trifluoropropyl)malonitrile), $CF_3(CF_2)_2CH_2C(CN)_2CH_2(CF_2)_3CF_2H$ (2-(2,2,3,3,4,4,4-heptafluorobutyl)-2-(2,2,3,3,4,4,5-octafluoropentyl)malonitrile), $CF_3CF_2CH_2C(CN)_2CH_2(CF_2)_3CF_2H$ (2-(2,2,3,3,4,4,5,5-octafluoropentyl)-2-(2,2,3,3,3-pentafluoropropyl)malonitrile), $CF_2HCF_2CF_2CF_2CH_2C(CN)_2CH_2CH_2CF_2CF_3$ (2-(2,2,3,3,4,4,5,5-octafluoropentyl)-2-(3,3,4,4,4-pentafluorobutyl)malodinitrile), $CF_3(CH_2)_2C(CN)_2CH_2(CF_2)_3CF_2H$ (2-(2,2,3,3,4,4,5,5-octafluoropentyl)-2-(3,3,3-trifluorobutyl)malonitrile);

The commercially available compounds of group B are listed, for example, in "The Pesticide Manual", thirteenth edition, British Crop Protection Council (2003), and other publications.

Lepimectin is known from Agro Project, PJB Publications Ltd, November 2004. Benclothiaz and its synthesis has been described in EP-A1 454621. Methidathion and paraoxon and their synthesis have been described in Farm Chemicals Handbook, Volume 88, Meister Publishing Company, 2001. Acetoprole and its synthesis have been described in WO 98/28277. Metaflumizon and its synthesis have been described in EP-A1 462 456. Flupyrazofos has been described in Pesticide Science 54, 1988, p. 237-243 and in U.S. Pat. No. 4,822,779. Pyrafluprole and its synthesis have been described in JP 2002193709 and in WO 01/00614. Pyriprole and its synthesis have been described in WO 98/45274 and in U.S. Pat. No. 6,335,357. Amidoflumet and its synthesis have been described in U.S. Pat. No. 6,221,890 and in JP 21010907. Flufenerim and its synthesis have been described in WO 03/007717 and in WO 03/007718. AKD 1022 and its synthesis have been described in U.S. Pat. No. 6,300,348. Chloranthraniliprole has been described in WO 01/70671, WO 03/015519 and WO 05/118552. Cyantraniliprol has been described in WO 01/70671, WO 04/067528 and WO 05/118552. Further anthranilamide derivatives have been described in WO 01/70671, WO 04/067528 and WO 05/118552. Cyflumetofen and its synthesis have been described in WO 04/080180. The aminoquinazolinone compound pyrifluquinazone has been described in EP A 109 7932. Sulfoximine derivatives such as sufloxaflor and analogues thereof, including their synthesis, have been described in WO 2006/060029 and WO 2007/149134. The alkynyl ether compounds have been described, for example, in JP 2006131529. Organosulfur compounds have been described in WO 07/060,839. The malonitrile compounds have been described in WO 02/089579, WO 02/090320, WO 02/090321, WO 04/006677, WO 05/068423, WO 05/068432 and WO 05/063694.

Examples of active substances with herbicidal activity are mentioned in groups C.1 to C.15:

C.1 Lipid biosynthesis inhibitors such as, for example, chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, di-allate, dimepiperate, EPTC, esprocarb, ethiolate, isopolinate, methiobencarb, molinate, orbencarb, pebulate, prosulfocarb, sulf-allate, thiobencarb, tiocarbazil, tri-allate, vernolate, benfuresate, ethofumesat and bensulid;

C.2 ALS inhibitors such as, for example, amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;

C.3 Photosynthesis inhibitors such as, for example, atraton, atrazine, ametryn, aziprotryn, cyanazine, cyanatryn, chlorazine, cyprazin, desmetryn, dimethametryn, dipropetryn, eglinazine, ipazine, mesoprazine, methometon, methoprotryn, procyazine, proglinazine, prometon, prometryn, propazine, sebuthylazine, secbumeton, simazine, simeton, simetryn, terbumeton, terbuthylazine, terbutryn, trietazine, ametridione, amibuzine, hexazinon, isomethiozine, metamitron, metribuzine, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezine, methazole, bentazone, propanil, pentanochlor, pyridate and pyridafol;

C.4 Protoporphyrinogen IX oxidase inhibitors such as, for example, acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidonethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazole, flufenpyr, flupropacil, nipyraclofen and etnipromid;

C.5 Bleacher herbicides such as, for example, metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethyl-phenoxy)-2-(4-trifluoromethylphenyl)pyrimidine and 3-heterocyclyl-substituted benzoyl derivatives of the formula II (see WO 96/26202, WO 97/41116, WO 97/41117 and WO 97/41118)

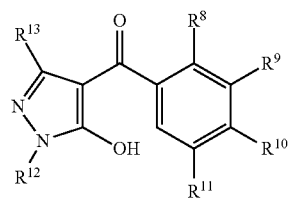

(II)

in which the variables $R^8$ to $R^{13}$ have the following meanings:

$R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfinyl or $C_1$-$C_6$-alkylsulfonyl;

$R^9$ is a heterocyclic radical selected from the group consisting of thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, it being possible for the abovementioned nine radicals to be unsubstituted or mono- or polysubstituted, for example mono-, di-, tri- or tetrasubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$ is hydrogen, halogen or $C_1$-$C_6$-alkyl;

$R^{12}$ is $C_1$-$C_6$-alkyl;

$R^{13}$ is hydrogen or $C_1$-$C_6$-alkyl.

C.6 EPSP synthase inhibitors such as, for example, glyphosate;

C.7 Glutamine synthase inhibitors such as, for example, glufosinate and bilanaphos;

C.8 DHP synthase inhibitors such as, for example, asulam;

C.9 Mitosis inhibitors such as, for example, benfluralin, butralin, dinitramin, ethalfluralin, fluchloralin, isopropalin, methalpropalin, nitralin, oryzalin, pendimethalin, prodiamin, profluralin, trifluralin, amiprofosmethyl, butamifos, dithiopyr, thiazopyr, propyzamide, tebutam, chlorthal, carbetamide, chlorbufam, chlorpropham and propham;

C.10 VLCFA inhibitors such as, for example, acetochlor, alachlor, butachlor, butena-chlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamide, napropamide, naproanilide, pethoxamid, flufenacet, mefenacet, fentrazamide, anilofos, piperophos, cafenstrol, indanofan and tridiphane;

C.11 Cellulose biosynthesis inhibitors such as, for example, dichlobenil, chlorthiamid, isoxaben and flupoxam;

C.12 Uncoupler herbicides such as, for example, dinofenate, dinoprop, dinosam, dinoseb, dinoterb, DNOC, etinofen and medinoterb;

C.13 Auxin herbicides such as, for example, clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr and benazoline;

C.14 Auxin transport inhibitors such as, for example, naptalam and diflufenzopyr;

C.15 benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

Suitable safeners can be selected from among the following list:

benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalenic anhydride, 2,2,5-trimethyl-3-(dichloroacetyl)-1,3-oxazolidine (R-29148), 4-(dichloroacetyl)-1-oxa-4-azaspiro[4.5]decane (AD-67; MON 4660) and oxabetrinil.

Examples of growth regulators are 1-naphthylacetamide, 1-naphthylacetic acid, 2-naphthyloxyacetic acid, 3-CPA, 4-CPA, ancymidole, anthraquinone, BAP, butifos; tribufos, butralin, chlorflurenol, chlormequat, clofencet, cyclanilide, daminozide, dicamba, dikegulac-sodium, dimethipin, chlorfenethol, etacelasil, ethephon, ethychlozate, fenoprop, 2,4,5-TP, fluoridamid, flurprimidol, flutriafol, gibberellic acid, gibberellin, guazatine, indolebutyric acid, indoleacetic acid, karetazan, kinetin, lactidichlor-ethyl, maleic hydrazide, mefluidide, mepiquat-chloride, naptalam, paclobutrazole, prohexadione-calcium, quinmerac, sintofen, tetcyclacis, thidiazuron, triiodobenzoic acid, triapenthenol, triazethan, tribufos, trinexapac-ethyl and uniconazole.

With a view to the treatment of seed, the plant protectants are preferably selected from among organic substances which have a fungicidal, insecticidal, acaricidal and/or nematicidal activity. In particular, they are one or more of the following substances:

Fungicidally active substances, for example fungicides of group A.1, in particular azoxystrobin, kresoxim-methyl, orysastrobin, pyraclostrobin or trifloxystrobin, fungicides of group A.2, in particular dimethomorph, carboxin, silthiofam, but also N-biphenylamides such as boscalid, bixafen or N-(3',4',5'-trifluorobiphenyl-2-yl)-3-difluoromethyl-1-methylpyrazole-4-carboxamide, fungicides of group A.3, in particular benomyl, carbendazim, hymexazole, imazalil, prochloraz, thiabendazole, but also triazoles such as, for example, difenoconazole, epoxiconazole, fluquinconazole, flutriafol, metconazole, prothioconazole, tebuconazole, triadimenol or triticonazole, furthermore metalaxyl, metalaxyl-M (mefenoxam), oxadixyl, guazatine, pyrimethanil, streptomycin, iprodione, fludioxonil or captan.

Insecticidally or acaricidally or nematicidally active substances, for example acetamiprid, alpha-cypermethrin, beta-cypermethrin, bifenthrin, carbofuran, carbosulfan, clothianidin, cyclorprothrin, cyfluthrin, cypermethrin, deltamethrin, diflubenzuron, dinotefuran, etofenprox, fenbutatin oxide, fenpropathrin, fipronil, flucythrinate, imidacloprid, lambda-cyhalothrin, nitenpyram, pheromones, spinosad, teflubenzuron, tefluthrin, terbufos, thiacloprid, thiamethoxam, thiodicarb, tralomethrin, triazamate, zeta-cypermethrin, spirotetramate, flupyrazofos, NC 512, tolfenpyrad, flubendiamide, bistrifluoron, benclothiaz, DPX-E2Y45, HGW86, pyrafluprole, pyriprole, F-7663, F-2704, amidoflumet, flufenerim or cyflumetofen.

The abovementioned plant protectants may be employed alone or in combination with one another.

In a preferred embodiment of the invention, the at least one plant protectant a) has a melting point of no more than 120° C., preferably no more than or less than 100° C.

In a further preferred embodiment the formulations according to the invention comprise at least one plant protectant a), which is a fungicide which, according to an especially preferred embodiment, is selected from among prochloraz, boscalid, pyraclostrobin, triticonazole, pyrimethanil, fluquinconazole and N-(3',4',5'-trifluorobiphenyl-2-yl)-3-difluoromethyl-1-methylpyrazole-4-carboxamide.

In an especially preferred embodiment, the formulation according to the invention comprises at least one fungicidal active substance from group A.1, for example at least one active substance selected among azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]-benzyl)carbamate, methyl (2-chloro-5-[1-(6-methylpyridin-2-ylmethoxyimino)ethyl]-benzyl) carbamate and methyl 2-(ortho-((2,5-dimethylphenyloxymethylene)phenyl)-3-methoxyacrylate, and in particular pyraclostrobin.

In a further especially preferred embodiment, the formulation according to the invention comprises at least one fungicidal active substance from group A.3, in particular at least one triazole and/or imidazole, for example at least one active substance selected among bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, cyazofamid, imazalil, pefurazoate, prochloraz and triflumizole.

In a further especially preferred embodiment, the formulation according to the invention comprises at least one fungicidal active substance from group A.1, which is preferably selected among azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]-benzyl)carbamate, methyl (2-chloro-5-[1-(6-methylpyridin-2-ylmethoxyimino)ethyl]benzyl)carbamate and methyl 2-(ortho-((2,5-dimethylphenyloxymethylene)phenyl)-3-methoxyacrylate, which is preferably pyraclostrobin, and at least one further active substance from among group A.3, in particular at least one triazole and/or imidazole, for example at least one active substance selected among bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, cyazofamid, imazalil, pefurazoate, prochloraz and triflumizole, in particular triticonazole or prochloraz or a mixture of triticonazole and prochloraz.

The formulations according to the invention comprise the at least one organic plant protectant a) as a rule in a concentration of from 0.1 to 40% by weight, frequently 1 to 30% by weight, in particular 2 to 25% by weight or 5 to 20% by weight, based on the total weight of the formulation. In the case of several plant protectants a), the total concentration of the plant protectants is, as a rule, in the range of from 0.1 to 40% by weight, frequently in the range of from 1 to 30% by weight and in particular in the range of from 2 to 25% by weight or in the range of from 5 to 20% by weight, based on the total weight of the formulation.

Furthermore, the formulations according to the invention comprise water. As regards the total weight of the undiluted formulation, the amount of water is, as a rule, in the range of from 1 to 80% by weight, frequently in the range of from 5 to 50% by weight, in particular in the range of from 10 to 40% by weight and preferably in the range of from 15 to 30% by weight. It is obvious that the amount of water and the amounts of the remaining constituents total 100% by weight.

In a preferred embodiment of the invention, the aqueous formulations comprise:

a. from 0.1 to 40% by weight, frequently from 1 to 30% by weight, in particular from 2 to 25% by weight or 5 to 20% by weight, of at least one organic plant protectant with a water solubility of less than 5 g/l at 20° C., as defined above, in particular at least one of the preferred or especially preferred plant protectants a);

b. from 1 to 60% by weight, frequently from 10 to 40% by weight, in particular 15 to 35% by weight, of at least one solvent b) as defined above, in particular at least one of the solvents b) specified as being preferred or especially preferred;

c. from 1 to 60% by weight, frequently from 10 to 40% by weight, in particular 15 to 35% by weight, of at least one solvent c) as defined above, in particular at least one of the solvents c) specified as being preferred or especially preferred;

d. from 1 to 60% by weight, frequently from 5 to 45% by weight, in particular 10 to 35% by weight, of at least one solvent d) as defined above, in particular at least one of the solvents d) specified as being preferred or especially preferred;

e. from 0.5 to 30% by weight, frequently 2 to 25% by weight or 4 to 24% by weight, in particular 5 to 20% by weight, of at least one nonionic surfactant e) as defined above, in particular at least one of the surfactants e) specified as being preferred or especially preferred;

f. from 0.5 to 25% by weight, frequently 1 to 25% by weight or 1 to 20% by weight, in particular 5 to 15% by weight, of at least one anionic surfactant f) as defined above, in particular at least one of the surfactants f) specified as being preferred or especially preferred; and g. water to 100% by weight, for example in an amount of from 1 to 80% by weight, frequently in the range of from 5 to 50% by weight, in particular in the range of from 10 to 40% by weight and specifically in the range from 15 to 30% by weight.

The information given in % by weight relates in each case to the total weight of the formulation according to the invention.

What has been said before also applies as regards the weight ratios of components a-f), in particular as regards the total amount of surfactants e)+f), as regards the total amount of solvents b)+c)+d), as regards the total amount of surfactants e)+f) plus solvents b)+c)+d), as regards the ratio of the total amount of surfactants e)+f) to plant protectant a), as regards the ratio of the total amount of surfactants e)+f) to the total amount of solvents b)+c)+d), and as regards the ratio of the total amount of surfactants e)+f) plus solvents b)+c)+d) to plant protectant a).

Moreover, the formulations of the invention may comprise customary adjuvants such as, for example, antifoams (defoamers), preservatives (bactericides), colorants, stabilizers, thickeners, stickers, antifreeze agents and further substances conventionally used in aqueous pesticide formulations. The total amount of these adjuvants will, as a rule, not amount to more than 20% by weight, in particular not to more than 15% by weight, of the weight of the undiluted formulation. The amount of an individual adjuvant will usually not exceed 5% by weight and in particular 3% by weight, with the exception of antifreeze agents and colorants.

Suitable antifoams comprise polysiloxanes, such as, for example, polydimethylsiloxane, long-chain alcohols, organofluorine compounds, fatty acids and their salts, and mixtures of these. Antifoams are usually employed in amounts of from 0.1 to 5 grams per liter of the formulations.

Suitable preservatives for avoiding bacterial infection of the compositions according to the invention comprise form aldehyde, alkyl esters of para-hydroxybenzoic acid, sodium benzoate, 2-bromo-2-nitropropane-1,3-diol, ortho-phenylphenol, dichlorophene, benzyl alcohol hemiformal, thiazolinone and isothiazolinone derivatives such as, for example, alkylisothiazolinones and benzisothiazolinones, 5-chloro-2-methyl-4-isothia-zolinone, pentachlorophenol, 2,4-dichlorobenzyl alcohol, and mixtures of these. Examples of suitable commercially available bactericidal products are Proxel® (ICI), Acticide® RS (Thor Chemie), Kathon® (Rohm & Haas) and Acticide MBS (Thor Chemie). As a rule, the amount of preservative will be from 0.1 to 10 grams per liter of the formulations.

Examples of colorants are both pigments, which are sparingly soluble in water, and dyes, which are soluble in water. Examples which may be mentioned are the dyes known by the names Rhodamin B, C.I. Pigment Red 112 and C.I. Solvent Red 1, and pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, acid red 18, food red 1, food red 2 and food red 7.

Suitable stabilizers comprise, for example, UV absorbents such as, for example, cinnamic acid esters, 3,3-diphenyl-2-cyanoacrylates, hydroxyl- and/or alkoxy-substituted benzophenones, N-(hydroxyphenyl)-benzotriazoles, hydroxyphenyl-s-triazines, oxalamides and salicylates, for example UVINUL® 3000, 3008, 3040, 3048, 3049, 3050, 3030, 3035, 3039, 3088, UVINUL® MC80, and free-radical scavengers such as, for example, ascorbic acid, citric acid, sterically hindered amines (known as HALS compounds) such as, for example, UVINUL® 4049H, 4050H, 5050H and the like, and antioxidants such as vitamin E. In a preferred embodiment, the stabilizer is citric acid or ascorbic acid. Usually, the amount of stabilizer will be in the range of from 0.01 to 10 grams per liter of formulation.

Examples of thickeners (i.e. compounds which impart a modified flow behavior to the formulation, i.e. high viscosity at rest and low viscosity in the agitated state) are polysaccharides such as xanthan gum (Kelzan®, Kelco), Rhodopol® 23 (Rhone Poulenc) or Veegum® (R.T. Vanderbilt) and organic and inorganic layer minerals such as Attaclay® (Engelhardt).

Examples of stickers, or adhesives, are ethylene oxide or propylene oxide block polymer surfactants and also polyvinyl alcohols, polyvinyl acetates, partially hydrolyzed polyvinyl acetates, polyvinylpyrrolidones, polyacrylates, polymethacrylates, polybutenes, polyisobutenes, polystyrenes, polyethylenamines, polyethylenamides, polyethylenimines (Lupasol®, Polymin®), polyethers and copolymers which are derived from the abovementioned polymers.

Examples of suitable antifreeze agents are $(C_1-C_4)$-alkanols such as ethanol, isopropanol, n-butanol, isobutanol, and also $(C_2-C_6)$-polyols such as glycerol, ethylene glycol, hexylene glycol and propylene glycol, and mixtures of these.

These customary additives can already be added during the preparation of the compositions according to the invention or, alternatively, only upon, or after, dilution with water for the preparation of the ready-to-use composition.

As a rule, the formulations of the present invention can be prepared by simply mixing the constituents until an apparently homogeneous fluid has been formed. The order in which the constituents are added is usually of minor importance. For example, the constituents may be put into a container and the mixture thus obtained is homogenized, for example by stirring, until a homogeneous liquid has formed.

However, it is also possible first to dissolve the organic plant protectants in at least one of the solvents b), c) and/or d) or a mixture of these solvents with at least one of the surfactants e) and to mix the resulting solution with water and the remaining constituents, for example by adding the solution to the water, or by adding the water to the solution. The temperature during mixing and the further mixing conditions are of minor importance. Usually, mixing of the constituents is carried out at temperatures of from 10° C. to 90° C., in particular from 10° C. to 60° C. Higher temperatures, for example 35° C. or 40° C. or higher may be expedient to accelerate the formation of the formulation. On the other hand, mixing can, as a rule, also be carried out at lower temperatures, approximately at 10° C. to 35° C.

Depending on the nature of the plant protectant employed, the formulations according to the invention are useful for controlling a large number of pests and can be employed both for the treatment of crops of plants and of seed and of inanimate material and for domestic purposes.

In the present context, "pests" or "harmful organisms" are understood as meaning all types of pests which can be combated or controlled using organic plant protectants, i.e. pesticides, in particular fungicides and mixtures of fungicides with other pesticides. The term pest therefore comprises plant-harming organisms, in particular harmful fungi and their spores, but also harmful insects, arachnids, nematodes and harmful plants. The term "control" comprises not only the curative treatment, i.e. the treatment of infected plants with the formulation according to the invention, but also the protective treatment, i.e. the treatment of plants by way of protection from infection with pests.

The present invention therefore also relates to:

use of formulations described herein for controlling pests, in particular plant pests; and methods of controlling harmful organisms, in particular plant-harming organisms, comprising the bringing into contact of harmful organisms, of their habitat, of their hosts, such as plants and seed, and of the soil, the area and the environment in which they grow or might grow, but also of materials, plants, seeds, soil, surfaces or spaces which are to be protected from attack by, or infection with, plant-harming organisms, with an effective amount of the formulations according to the invention.

A further aspect of the invention relates to the use of the formulations described herein for protecting plants, including seed, in particular for protecting useful plants against attack by harmful organisms. The present invention thus also relates to the use of the formulations for controlling phytopathogenic organisms such as, for example, harmful fungi, insects, arachnids, nematodes and harmful plants. In accordance with a preferred embodiment, the invention relates to the use of the formulations for protecting seed from attack by harmful fungi, insects, arachnids and nematodes, in particular from attack by harmful fungi.

The formulations according to the invention can be applied in undiluted form or as a dilution with water. According to a preferred embodiment, the formulations are employed in undiluted form. In a further preferred embodiment, the formulations are diluted before application with up to 50 parts of water, preferably with up to 10 parts of water and in particular with up to 3 parts of water per part of the formulations, all parts meaning parts by weight.

Dilution is usually effected by pouring the formulations according to the invention into the water. Usually, agitation, such as, for example, stirring, is employed for rapidly mixing the concentrate with water. However, agitation is not necessary as a rule. Although the temperature is not a critical factor for the dilution process, dilutions are usually carried out at temperatures in the range of from 0° C. to 50° C., in particular at 10° C. to 30° C., or at ambient temperature.

The water employed for diluting is, as a rule, tap water. However, the water may already comprise water-soluble compounds which are used in plant protection, such as, for example, nutrients, fertilizers or pesticides.

The formulations of the invention, optionally in dilute form, are employed or applied using methods and devices known to the skilled worker. In particular, they may be employed for treating seed by customary seed-treatment techniques, for example by seed dressing, seed coating, seed soaking, seed film coating, seed multilayer coating, seed encrusting, seed dripping, seed dusting and by seed pelleting.

In accordance with a first embodiment of the seed treatment, the seed, i.e. those parts of the plant which are capable of propagation and which are intended for sowing, are treated with a formulation according to the invention or an aqueous dilution thereof. In the present context, the term seed comprises seeds and any type of plant part capable of propagation, including seeds, seed grains, parts of seeds, suckles, fruits, tubers, cereal grains, cuttings or the like, in particular grains and seeds.

The treatment of the seed can be effected for example by mixing, spraying or fogging the seed with a plant protection formulation according to the invention or with a spray mixture obtained therefrom by dilution with water, prior to sowing and before the plants emerge. These measures can be carried out in specific devices for the treatment of seed, for example in seed drills. However, the treatment is also possible simply by mixing an aqueous formulation according to the invention with the seed in a container, for example a bucket or a tray, and then allowing the seeds to dry.

Alternatively, the seed may also be treated with the plant protection formulation according to the invention during sowing.

In a further embodiment of the seed treatment or soil treatment according to the invention, the formulation according to the invention will be introduced into furrows which already comprise the seed. Alternatively, it is also possible first to treat the seed furrow with the formulation according to the invention and then to introduce the seed into the seed furrow.

In a further embodiment of the invention, grown plants are treated with the formulations, in particular by spraying. To this end, it is possible to apply the formulations to the plants in undiluted form or in the form of an aqueous dilution.

In general, the way in which a formulation according to the invention is applied should depend on the intended purpose; in any case, as fine as possible a distribution of the plant protectants present in the formulation should be ensured.

The amounts of formulation of the invention employed for the treatment of seed should be selected such that the seed comes into contact with an effective amount of the plant protectants present in the formulation. In general, an amount of a formulation according to the invention which comprises from 0.1 g to 10 kg, in particular from 1 g to 5 kg and specifically from 1 g to 2.5 kg of the plant protectant or of a mixture of such active substances per 100 kg of seed. For certain useful plants such as, for example, lettuce and onions, the amounts of active substance to be employed may be greater.

Depending on the nature of the active substance employed, the formulations according to the invention are suitable for the treatment of seed of any useful plants, for example grain crops, root crops, oil crops, vegetables, spices, ornamentals and the like, for example for the treatment of seed of the following plants: durum wheat and other wheat species, oats, rye, barley, maize, including fodder maize and sugar maize, soybeans, brassicas, cotton, sunflower, bananas, rice, oilseed rape, beet, sugarbeet, fodder beet, aubergines, potatoes, turf, grass seed, tomatoes, leek, pumpkin/squash, cabbage, lettuces, bell peppers, cucumbers, melons, beans, peas, garlic, onions, carrots, tobacco, grapes, petunias, geraniums, pelargoniums, pansies, and the like.

The formulations according to the invention are also suitable for treating the seed of useful plants which are resistant to herbicides, fungicides, insecticides or nematicides as the result of methods based on breeding, mutation and/or genetic engineering. For example, formulations can be employed for treating the seed of transgenic plants which are resistant to herbicides from the group consisting of the sulfonylureas (EP A 0 257 993, U.S. Pat. No. 5,013,659), the imidazolinones (cf., for example, U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), the glufosinates and related compounds (cf., for example, EP-A-0 242 236, EP-A-242 246) and the glyphosates and related compounds (cf., for example, WO 92/00377), or for treating seed of plants which are resistant to herbicides selected from the group of the cyclohexadienone/aryloxyphenoxypropionic acid herbicides ( U.S. Pat. Nos. 5,162,602, 5,290,696, 5,498,544, 5,428,001, 6,069,298, 6,268,550, 6,146,867, 6,222,099, 6,414,222 ) or for treating seed of transgenic useful plants such as, for example, cotton and maize, which have the ability of producing *Bacillus thuringiensis* toxins (Bt toxins), which confer resistances to certain pests (EP A 0 142 924, EP A 0 193 259).

The formulations of the invention may furthermore be employed for treating the seed of plants whose properties are modified over existing plants and which can be generated for example with the aid of traditional breeding methods and/or mutations or by recombinant methods. Thus, the generation of recombinant variants of crop plants has been described repeatedly, the purpose being to modify the starch of these plants (for example WO 92/11376, WO 92/14827, WO 91/19806) or to modify the fatty acid composition of the plants (WO 91/13972).

The seed which has been treated in accordance with the invention is distinguished by advantageous properties in comparison with traditionally treated seed and is therefore also subject matter of the present application.

The examples which follow are intended to illustrate the invention.

I. Preparation of Formulations (General Protocol)

The components detailed in table 1 were employed.

Components a) to f) correspond to components a) to f) of the formulations according to the invention.

Explanation of Trade Names:

Edenor® TI 05: Fatty acid mixture with a high oleic acid content (Cognis),

Agnique® KE 3658: Fatty acid dimethyl amides (Cognis);

Agrisol PX401: 2-phenoxyethanol (Akzo Nobel);

Solvesso® 150 ND: Predominantly $C_{10}$- and $C_{11}$-alkylbenzenes with a boiling range of from 175 to 209° C., naphthalene-depleted (ExxonMobil Chemical);

Solvesso® 200 ND: Predominantly $C_{10}$- and $C_{14}$-alkylnaphthalenes with a boiling range of from 235 to 305° C., naphthalene-depleted (ExxonMobil Chemical);

Lutensol® TO5: C13-oxo alcohol polyethoxylate with 5 ethylene oxide (EO) units, HLB value: 10.5 (BASF);

Lutensol® TO7: C13-oxo alcohol polyethoxide having 7 EO units, HLB value 12.0 (BASF);

Lutensol® TO15: C13-oxo alcohol polyethoxide having 15 EO units, HLB value 15.5 (BASF);

Lutensol® XP50: 2-propylheptanol polyethoxylate with 5 EO units, HLB value: 11.5 (BASF);

Lutensol® XP140: 2-propylheptanol polyethoxylate with 14 EO units, HLB value: 16.0 (BASF);

Soprophor® S 25: Tristyrylphenol polyethoxylate having 25 EO units, HLB value: 14.5 (Rhodia);

S-MAZ® 20: Sorbitan monofatty acid ester (mainly monododecanoate), HLB value: 8.0 (BASF);

T-MAZ® 20: polyethoxylated sorbitan monolaurate with approximately 20 EO units, HLB value: 16.7 (BASF);

Pluronic PE 6400: Propylene oxide/ethylene oxide block polymer with approximately 40% EO content (BASF);

Lutensit® A-BO: Sodium 2-sulfonyldioctylsuccinate (BASF);

Soprophor® DSS 15: ethoxylated distyrylphenol sulfate with 15 EO units (Rhodia);

Soprophor® 4D 384: ethoxylated tristyrylphenol ammonium sulfate with 16 EO units (Rhodia).

Rhodiasolv® DIB: mixture of diisobutyl glutarate, diisobutyl succinate and diisobutyl adipate (Rhodia).

Formulations 1 to 23 according to the invention are listed in table 2. Table 2 also shows the components and their amounts which have been employed for the preparation of the respec-

TABLE 1

Components a) to f) of the formulations listed in table 2 by way of example.

| a) | b)* | c)* | d)** | e) | f) |
|---|---|---|---|---|---|
| prochloraz | γ-butyrolacton (miscible) | Acetophenon (5.5 g/l) | Agnique ® KE 3658 | Lutensol ® TO5 | Lutensit ® A-BO |
| pyraclostrobin | Arcosolv ® PMA (1-methoxy-2-propanol acetate)(400 g/l) | Agrisol PX401 (24 g/l) | Edenor ® TI 05 | Lutensol ® TO7 | Soprophor ® DSS 15 |
| triticonazole | hexylene glycol (500 g/l) | benzyl alcohol (39 g/l) | Solvesso ® 150 ND | Lutensol ® TO15 | Soprophor ® 4D 384 |
|  | Purasolv ® NPL (n-propyl lactate) (miscible) | butylene carbonate | Solvesso ® 200 ND | Lutensol ® XP50 |  |
|  | DMSO (miscible) | triacetin (64 g/l) | Dodecanol | Lutensol ® XP140 |  |
|  | tetrahydro-furfuryl alcohol (miscible) | cyclohexanone (24 g/l) | Rhodiasolv ® DIB | Pluronic PE 6400 |  |
|  |  | 2-heptanone (4.3 g/l) | 2-ethylhexyl lactate | S-MAZ ® 20 |  |
|  |  |  |  | Soprophor ® S 25 |  |
|  |  |  |  | T-MAZ ® 20 |  |

*The solubility in water at 20° C. of the solvent in question is indicated in parentheses. Miscible means fully miscible with water.
**All solvents of group d) have a solubility in water of less than 0.1 g/l at 20° C.

tive formulations. The preparation was carried out as described hereinbelow, all steps having been carried out at room temperature (RT):

One or more components of component A were placed into a container, and, after three or more components B, C and D had been added, the mixture was stirred until A was dissolved as completely as possible. Thereafter, two or more components E and F were added, with careful stirring, and stirring was continued until as homogeneous as possible a solution was obtained. Thereafter, the distilled water was added, with stirring, and the mixture was stirred until a clear formulation was obtained.

II. Stability Tests of the Formulations According to the Invention

The formulations prepared were left to stand overnight at RT, and their appearance was then determined macroscopically. A homogeneous and clear fluid suggested that the microemulsion had remained stable, while a cloudy or milky appearance would have suggested a markedly increased droplet size and, possibly, the conversion of the microemulsion into an ordinary emulsion.

Thereafter, the formulations were stored for in each case 3 days at −10° C. or 54° C. and then checked macroscopically as described above. Again, a clear, homogeneous appearance showed whether the microemulsions are stable under these conditions. The formation of schlieren was considered a sign for the possibility that prolonged storage of the formulation under the given conditions might lead to phase separation. The freezing of the formulation suggests a relatively high freezing point, which could be lowered for example by adding an antifreeze agent.

The results are compiled in table 2.

TABLE 2

Preparation and stability of the formulations

| | Serial No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Pyraclostrobin | | | | | | | | 10.0 g | 10.0 g | 10.0 g | 10.0 g | 10.0 g |
| Prochloraz | 5.0 g | 5.0 g | 5.0 g | 15.0 g | 15.0 g | 10.0 g | 15.0 g | | | | | |
| DMSO | 2.5 g | 2.5 g | 2.5 g | 2.5 g | 2.5 g | | | | | | | |
| Arcosolv PMA | | 20.0 g | 20.0 g | 20.0 g | 20.0 g | | | | | | | |
| Hexylene glycol | | | | | | 10.0 g | 10.0 g | 15.0 g | 15.0 g | 15.0 g | 15.0 g | 15.0 g |
| Purasolv NPL | 20.0 g | | | | | | | | | | | |
| Acetophenone | 20.0 g | 20.0 g | | 15.0 g | | | | | | | | |
| Benzyl alcohol | | | | | | | | 17.5 g | 17.5 g | 17.5 g | 17.5 g | 17.5 g |
| Butylene carbonate | | | | | | | | | | | | |
| Cyclohexanone | | | 20.0 g | | 15.0 g | 17.5 g | 17.5 g | | | | | |
| Agnique KE 3658 | 10.0 g | 10.0 g | 10.0 g | 10.0 g | | | | | | | | |
| Edenor TI 05 | | | | | 10.0 g | | | | | | | |
| Solvesso 150 ND | | | | | | 17.5 g | 17.5 g | | | | | |
| Solvesso 200 ND | | | | | | | | 17.5 g | 17.5 g | 17.5 g | 17.5 g | 17.5 g |
| Lutensit A-BO | | | | | | 5.4 g | 5.4 g | | | | | |
| Lutensol TO 5 | | | | | | | | | | 3.6 g | | |
| Lutensol TO 7 | 7.2 g | 7.2 g | 7.2 g | 7.2 g | 7.2 g | | | | | | | |
| Lutensol TO 15 | | | | | | | | | 3.6 g | | | |
| Lutensol XP 50 | | | | | | | | | 3.6 g | | | |
| Lutensol XP 140 | | | | | | | | | 3.6 g | | | |
| Pluronic PE 6400 | | | | | | | | | | | | 7.2 g |
| S-Maz 20 | | | | | | | | | | | | |
| Soprophor 4D384 | 7.2 g | 7.2 g | 7.2 g | 7.2 g | 7.2 g | | | 10.8 g | 10.8 g | 10.8 g | 10.8 g | 10.8 g |
| Soprophor S 25 | 3.6 g | 3.6 g | 3.6 g | 3.6 g | 3.6 g | 12.6 g | 12.6 g | | | 7.2 g | | |
| T-Maz 20 | | | | | | | | | | | 7.2 g | |
| Water | 24.5 g | 24.5 g | 24.5 g | 19.5 g | 19.5 g | 27.0 g | 22.0 g | 22.0 g | 22.0 g | 22.0 g | 22.0 g | 22.0 g |
| Stability after 1 d | clear | clear | clear | clear | clear | clear | clear | clear | clear | clear | clear | clear |
| −10° C., 3 d | clear | clear | clear | clear | clear | clear | clear | clear | clear | clear | clear | clear |
| +54° C., 3 d | schlieren | clear | clear | clear | clear | clear | clear | clear | clear | clear | clear | clear |

| | Serial No. | | | | | | | | | | |
|---|---|---|---|---|---|---|---|---|---|---|---|
| | 13 | 14 | 15 | 16 | 17 | 18 | 19 | 20 | 21 | 22 | 23 |
| Pyraclostrobin | 10.0 g | 10.0 g | 10.0 g | 10.0 g | 10.0 g | 10.0 g | 2.0 g | 2.0 g | 2.0 g | 2.0 g | 2.0 g |
| Prochloraz | | | | | | | 6.9 g | 6.9 g | 6.9 g | 6.9 g | 6.9 g |
| Triticonazole | | | | | | | 1.5 g | 1.5 g | 1.5 g | 1.5 g | 1.5 g |
| DMSO | | | | | | | 2.5 g | 2.5 g | 2.5 g | 2.5 g | 2.5 g |
| Hexylene glycol | 15.0 g | 15.0 g | 15.0 g | 15.0 g | 15.0 g | 15.0 g | 20.0 g | 20.0 g | 20.0 g | | 20.0 g |
| Purasolv NPL | | | | | | | | | | 20.0 g | |
| Acetophenone | | | | 17.5 g | 17.5 g | 17.5 g | | | | | |
| Agrisol PX 401 | | | | | | | | 15.0 g | 15.0 g | | |
| Benzyl alcohol | 17.5 g | 17.5 g | 17.5 g | | | | | | | | |
| Butylene carbonate | | | | | | 15.0 g | | | | | |
| Triacetin | | | | | | | | | | 15.0 g | 15.0 g |
| Agnique KE 3658 | | | | | | | 10.0 g | 10.0 g | | 10.0 g | 10.0 g |
| 1-Dodecanol | | | | | | | | | 10.0 g | | |
| Solvesso 150 ND | | | | 17.5 g | 17.5 g | 17.5 g | | | | | |
| Solvesso 200 ND | 17.5 g | 17.5 g | 17.5 g | | | | | | | | |
| Lutensit A-BO | | | | 7.2 g | 7.2 g | | | | | | |
| Lutensol TO 5 | | 3.6 g | | | | 3.6 g | | | | | |
| Lutensol TO 7 | | | | | | | 7.2 g | 7.2 g | 7.2 g | 7.2 g | 7.2 g |
| Lutensol TO 15 | | | | | 10.8 g | 3.6 g | | | | | |

TABLE 2-continued

Preparation and stability of the formulations

| | | | | | | | | | | | |
|---|---|---|---|---|---|---|---|---|---|---|---|
| Lutensol XP 50 | | | 3.6 g | | | | | | | | |
| Lutensol XP 140 | | | 3.6 g | | | | | | | | |
| Pluronic PE 6400 | | | | | | | | | | | |
| S-Maz 20 | 7.2 g | | | | | | | | | | |
| Soprophor 4D384 | 10.8 g | | | | 10.8 g | | 7.2 g | 7.2 g | 7.2 g | 7.2 g | 7.2 g |
| Soprophor DSS 15 | | 10.8 g | 10.8 g | | | | | | | | |
| Soprophor S 25 | | 3.6 g | | 10.8 g | | | 3.6 g | 3.6 g | 3.6 g | 3.6 g | 3.6 g |
| T-Maz 20 | | | | | | | | | | | |
| Water | 22.0 g | 22.0 g | 22.0 g | 22.0 g | 22.0 g | 22.0 g | 24.1 g | 24.1 g | 24.1 g | 24.1 g | 24.1 g |
| Stability after 1 d | clear | clear | clear | clear | clear | clear | clear | clear | clear | clear | clear |
| −10° C., 3 d | clear | clear | clear | clear | clear | clear | clear | clear | frozen | clear | clear |
| +54° C., 3 d | clear | clear | clear | clear | clear | clear | clear | clear | some schlieren | clear | clear |

| | Serial No. | | | | |
|---|---|---|---|---|---|
| | 24 | 25 | 26 | V1 | V2 |
| Pyraclostrobin | 12.0 g | 12.0 g | 12.0 g | | |
| Prochloraz | 44.1 g | 44.1 g | 44.1 g | 5.0 g | 15.0 g |
| Triticonazole | 16.0 g | 16.0 g | 16.0 g | | |
| DMSO | 25.0 g | 25.0 g | 25.0 g | 2.5 | 2.5 |
| Hexylene glycol | 200 g | | | | |
| Plurasolv NPL | | | | 20.0 g | |
| Tetrahydrofurfuryl alcohol | | 200 g | 200 g | | |
| Acetophenone | | | | 20.0 g | |
| Butylene carbonate | 150 g | | | | |
| Triacetin | | 150 g | 150 g | | 10.0 g |
| Agnique KE 3658 | | | | 10.0 g | |
| Edenor TI 05 | | 100 g | | | 32.5 g |
| Rodiasolv DIB | 100 g | | | | |
| 2-Ethylhexyl lactate | | | 100 g | | |
| Lutensit A-BO | | | | | |
| Lutensol TO 5 | 80 g | 80 g | 80 g | | 4.0 g |
| Lutensol TO 7 | | | | 18.0 g | |
| Soprophor 4D384 | 80 g | 80 g | 80 g | | |
| Soprophor DSS 15 | 10 g | 10 g | 10 g | | |
| Soprophor S 25 | | | | | 16.0 g |
| Red dye* | 40 g | 40 g | 40 g | | |
| Bacterizide** | 2 g | 2 g | 2 g | | |
| Water | 260.9 g | 260.9 g | 260.9 g | 24.0 g | 20.0 g |
| Stability after 1 d | clear | clear | clear | emulsion | emulsion |
| −10° C., 3 d | some schlieren | some schlieren | clear | n.d. | n.d. |
| +54° C., 3 d | schlieren | schlieren | schlieren | n.d. | n.d. |

*Acid Red 18
**Methylisothiazolinone/benzoisothiazolinone mixture: Acticide ® MBS, Thor GmbH, Speyer III. Examinations of Treated Seed The following formulations were used for comparative experiments:

Formulation V3: Abavit UF (BASF); this is a traditional seed-treatment formulation which comprises mainly the active substances carboxin and prochloraz and the organic solvent N-methylpyrrolidone. V3 was employed in undiluted form hereinbelow.

Formulation V4: Kinto Duo (BASF); this is a traditional aqueous seed-treatment suspension which comprises prochloraz and triticonazole. The formulations of Examples 24, 25 and 26 and commercial formulation V4 were employed hereinbelow in diluted form, with one part of water per part of the formulation.

A) Seed-Dressing (General Protocol)

Dressing was carried out with the formulations prepared by the above protocol as seed-dressing slurries. A seed-dressing machine from SATEC was used, in which the seed is mixed by the rotor-stator principle, and the seed-dressing slurry is sprayed by means of a spinning disk. The rotor speed is adjusted to 200 rpm, and the air flow of the machine was adjusted to 960 l/h at the pressure gauge of the compressed-air supply. The seed-dressing slurries used were the formulations prepared in accordance with the above protocol. The desired amount of seed-dressing slurry was metered using a hose pump, the end of the hose being fixed at a short distance above the spinning disk. The application rates for the commercial seed-dressing formulation V3 and the example formulations 19, 21 and 23 were in each case 2 ml/kg. The commercial seed-dressing formulation V4, which had been diluted with water in the ratio 1:1 v/v, and the formulations of Examples 24, 25 and 26, which had been diluted with water in the ratio 1:1 v/v were applied in each case at 4 ml/kg. The seed to be dressed was cleaned, if required, and conditioned for 24 hours in a controlled-environment cabinet at 20° C. and 50% atmospheric humidity to create more reproducible conditions. After 2 kg of the seed had been introduced into the machine, the spinning disk was switched on, and the seed-dressing was started by switching on the pump. After 30 seconds, the seed-dressing was ended by discharging the seed.

B) Examination of the Flowability

The time taken by the dressed seed for running out of a shaking funnel was determined and served as a measure for the flowability. To this end, all of the seed (2 kg) was placed immediately after dressing into the funnel whose flowing-out hole was 2.8 cm in diameter and which was shaken at an amplitude of 1.5 mm. Using this method, wheat seed treated with the formulations of examples 19, 21, 23, 24, 25 and 26 was compared with seed which had been treated with the commercial seed-dressing formulations V3 and V4. In all cases, seed dressed by the above method was employed.

The flow behavior results thus obtained are compiled in table 5.

TABLE 5

Comparison of the flow behavior of dressed wheat seed.

|  | Flowability (in relation to untreated seed) |
|---|---|
| untreated | 100% |
| Formulation V3 | 87% |
| Formulation V4 | 70% |
| Example 19 | 91% |
| Example 21 | 91% |
| Example 23 | 91% |
| Example 24 | 80% |
| Example 25 | 80% |
| Example 26 | 80% |

C) Examination of the Dust Development

The examinations were carried out one day after the above-described seed-dressing had been carried out, in the same seed-dressing machine. In the meantime, dressed seed was stored in a controlled-environment cabinet for 24 hours at 20° C. and 50% atmospheric humidity. The rotor speed and the air flow through the machine were set as described above, and the machine was left to run for 10 minutes for conditioning purposes. A previously weighed filter (Fisherbrand fiberglass filter 38 mm, product No. FB59403) was inserted into the lid of the seed-dressing machine by suction. Here, a vacuum pump took in a portion of the pressurized air passed through the machine, including any dust which may be generated. Then, with the pump and the rotor running, the machine was charged with 1 kg of seed, and the pump was stopped after 30 seconds. The filter was counterweighed, and the dust residue was thus determined in grams per 100 kg of seed.

Using this method, wheat grains dressed with the formulations of examples 19, 21, 23, 24, 25 and 26 were compared with those which had been treated with the commercial seed-dressing formulations V3 and V6. The dust-developments results thus obtained are compiled in table 6.

TABLE 6

Comparison of the dust development of treated wheat seed.

|  | Dust development [g/100 kg] |
|---|---|
| untreated | 0.46 |
| Formulation V3 | 0.05 |
| Formulation V4 | 0.86 |
| Example 19 | 0.01 |
| Example 21 | 0.04 |
| Example 23 | 0.03 |
| Example 24 | 0.00 |
| Example 25 | 0.00 |
| Example 26 | 0.00 |

We claim:

1. A stable homogeneous liquid aqueous plant protection formulation, comprising:
a) from 0.1 to 40% by weight of at least one organic plant protectant with a water solubility of less than 5 g/l at 20° C.;
b) from 10 to 40% by weight of at least one solvent with a water solubility of over 100 g/l at 20° C.;
c) from 10 to 40% by weight of at least one solvent with a water solubility of from 2 to 100 g/l at 20° C.;
d) from 5 to 45% by weight of at least one solvent with a water solubility of less than 2 g/l at 20° C.;
e) from 2 to 25% by weight of at least one nonionic surfactant;
f) from 1 to 25% by weight of at least one anionic surfactant; and
g) from 10 to 40% by weight of water;
wherein the at least one solvent d) is selected from the group consisting of aliphatic and cycloaliphatic hydrocarbons with boiling points of from 100 to 310° C., $(C_8-C_{20})$-alkylphenols, $(C_8-C_{20})$-alkanols, $(C_{10}-C_{20})$-alkanecarboxylic alkyl esters, $(C_9-C_{20})$-hydroxyalkanecarboxylic alkyl esters, $(C_{12}-C_{28})$-cycloalkanecarboxylic alkyl esters, $(C_{12}-C_{28})$-cycloalkanedicarboxylic dialkyl esters, $(C_{10}-C_{15})$-dialkyl dicarboxylates, $(C_{25}-C_{35})$-alkanetriol alkanoates, N-$(C_6-C_{18})$-alkyl-$(C_3-C_5)$-lactams, $(C_8-C_{26})$-fatty acids, their dialkyl amides and their alkyl esters.

2. The plant protection formulation of claim 1, wherein the at least one solvent b) is selected from the group consisting of hydroxylated (C4-C8)-alkanecarboxylic esters, aliphatic (C2-C8)-di- and -triols, (C5-C8)alkanecarboxylic alkoxyalkyl esters, dimethyl sulfoxide, tetrahydrofurfuryl alcohol, (C3-C4)-alkylene carbonates, N,N'-dimethyl-(C3-C4)-alkyleneureas, (C3-05)-lactones, N-methyl-(C3-05)-lactams and tri-(C1-C3)alkyl phosphates.

3. The plant protection formulation of claim 2, wherein the at least one solvent b) comprises dimethyl sulfoxide.

4. The plant protection formulation of claim 3, wherein the at least one solvent b) comprises at least one second solvent b) other than dimethyl sulfoxide.

5. The plant protection formulation of claim 1, wherein the at least one solvent c) is selected from the group consisting of (C5-C9)-alkanecarboxylic alkyl esters, (C9-C12)-alkanecarboxylic alkoxyalkyl esters, (C5-C9)-dialkyldicarboxylic esters, (C5-C9)-ketones, (C5-C9)-arylalkyl alcohols, (C5-C9)-aryloxyalkyl alcohols, (C5-C9)-cycloalkyl alcohols, (C5-C9)-alkanediol alkanoates, (C5-C9)-alkanetriol alkanoates and (C5-C6)-alkylene carbonates.

6. The plant protection formulation of claim 1, wherein the at least one nonionic surfactant e) is selected from the group consisting of monofatty acid esters of polyhydroxylated compounds and compounds which have at least one oligo-(C2-C4)-alkylene ether group.

7. The plant protection formulation of claim 6, wherein the at least one nonionic surfactant e) is selected from the group consisting of sorbitan monofatty acid esters, homo- or cooligomers of (C2-C4)-alkylene oxides, oligo-(C2-C4)-alkylene oxide (C8-C22)-alkyl ethers, oligo-(C2-C4)-alkylene oxide (C1-C16)-alkylbenzene ethers, oligo-(C2-C4)-alkylene oxide mono-, di- or tristyrylphenyl ethers and oligo-(C2-C4)-alkylene oxide mono- or distyrylphenyl ether/formaldehyde condensates.

8. The plant protection formulation of claim 1, wherein component e) comprises at least two nonionic surfactants with different HLB values.

9. The plant protection formulation of claim 8, wherein component e) comprises at least one nonionic surfactant with an HLB value of no more than 13 and at least one nonionic surfactant with an HLB value of above 13.

10. The plant protection formulation of claim 9, where the nonionic surfactant with an HLB value of no more than 13 is selected from oligo-(C2-C4)-alkylene (C8-C22)-alkyl ethers.

11. The plant protection formulation of claim 9, wherein the nonionic surfactant with an HLB value of above 13 is selected from the group consisting of propylene oxide/ethylene oxide block cooligomers, oligo-(C2-C3)-alkylene oxide (C8-C22)-alkyl ethers, oligo-(C2-C3)-alkylene oxide mono-, di- and tristyrylphenyl ethers.

12. The plant protection formulation of claim 1, wherein the at least one plant protectant a) has a melting point of no more than 120° C.

13. The plant protection formulation of claim 1, wherein the at least one plant protectant a) is a fungicide.

14. The plant protection formulation of claim 13, wherein the fungicide is selected from the group consisting of azoles, strobilurins and N-biphenylamides of heteroaromatic carboxylic acids.

15. The plant protection formulation of claim 14, wherein the fungicide is selected from the group consisting of prochloraz, boscalid, pyraclostrobin, triticonazole, pyrimethanil, fluquinconazole, N-(4'-bromobiphenyl-2-yl)-4-difluoromethyl-2-methylthiazole-5-carboxamide, N-(4'trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide and N-(3',4',5'-trifluorobiphenyl-2-yl)-3-difluoromethyl-1-methylpyrazole-4-carboxamide.

16. The plant protection formulation of claim 1, further comprising at least one organic colorant.

17. A method of treating seed comprising bringing-into-contact of the seed with an effective amount of an aqueous plant protection formulation as defined in claim 1.

18. The method of claim 17, wherein said bringing-into-contact is effected by spraying.

19. A treated seed obtainable by the method of claim 17.

20. A method of controlling plant-harming organisms, comprising the bringing-into-contact the plant-harming organisms, a plant, soil or an environment in which a plant grows, with an effective amount of the formulation as defined in claim 1.

* * * * *